(12) United States Patent
Akagishi et al.

(10) Patent No.: US 9,643,167 B2
(45) Date of Patent: May 9, 2017

(54) ZEOLITE-CONTAINING CATALYST AND METHOD FOR PRODUCING THE SAME, AND METHOD FOR PRODUCING PROPYLENE

(71) Applicant: ASAHI KASEI CHEMICALS CORPORATION, Tokyo (JP)

(72) Inventors: Kenji Akagishi, Tokyo (JP); Hiroyuki Yano, Tokyo (JP); Ryusuke Miyazaki, Tokyo (JP)

(73) Assignee: ASAHI KASEI CHEMICALS CORPORATION, Tokyo (JP)

( * ) Notice: Subject to any disclaimer, the term of this patent is extended or adjusted under 35 U.S.C. 154(b) by 36 days.

(21) Appl. No.: 14/628,179

(22) Filed: Feb. 20, 2015

(65) Prior Publication Data

US 2015/0165425 A1 Jun. 18, 2015

Related U.S. Application Data

(62) Division of application No. 12/995,803, filed as application No. PCT/JP2009/061560 on Jun. 25, 2009, now Pat. No. 8,993,469.

(30) Foreign Application Priority Data

Aug. 6, 2008 (JP) .............................. 2008-202806

(51) Int. Cl.

| B01J 29/06 | (2006.01) |
|---|---|
| C07C 1/20 | (2006.01) |
| C07C 2/00 | (2006.01) |
| C07C 4/00 | (2006.01) |
| C07C 5/00 | (2006.01) |
| B01J 29/70 | (2006.01) |
| B01J 21/08 | (2006.01) |
| B01J 29/40 | (2006.01) |
| B01J 35/02 | (2006.01) |
| B01J 37/00 | (2006.01) |
| C07C 6/04 | (2006.01) |

(52) U.S. Cl.
CPC .............. *B01J 29/70* (2013.01); *B01J 21/08* (2013.01); *B01J 29/06* (2013.01); *B01J 29/40* (2013.01); *B01J 35/023* (2013.01); *B01J 37/0045* (2013.01); *C07C 2/00* (2013.01); *C07C 6/04* (2013.01); *B01J 2229/42* (2013.01); *C07C 2521/08* (2013.01); *C07C 2529/40* (2013.01); *C07C 2529/70* (2013.01); *Y02P 20/52* (2015.11)

(58) Field of Classification Search
USPC .... 502/64, 71; 585/638, 639, 640, 502, 520, 585/648, 653
See application file for complete search history.

(56) References Cited

U.S. PATENT DOCUMENTS

| 3,308,069 | A | | 3/1967 | Wadlinger et al. | |
|---|---|---|---|---|---|
| 3,926,782 | A | | 12/1975 | Plank et al. | |
| 3,957,689 | A | | 5/1976 | Ostermaier et al. | |
| 4,207,208 | A | * | 6/1980 | Lucki ...................... | B01J 29/46 502/49 |
| 4,916,501 | A | | 4/1990 | Thenoz et al. | |
| 5,110,776 | A | | 5/1992 | Chitnis et al. | |
| 5,689,027 | A | * | 11/1997 | Abichandani ............ | B01J 29/40 585/481 |
| 6,022,471 | A | | 2/2000 | Wachter et al. | |
| 2006/0058562 | A1 | | 3/2006 | Choi et al. | |
| 2007/0293714 | A1 | | 12/2007 | Long et al. | |
| 2010/0197986 | A1 | * | 8/2010 | Midorikawa ............ | B01J 29/06 585/640 |

FOREIGN PATENT DOCUMENTS

| EP | 0 496 226 A1 | 7/1992 |
|---|---|---|
| EP | 0 837 118 A2 | 4/1998 |
| EP | 2 189 435 A1 | 5/2010 |
| JP | 46-10064 | 3/1971 |
| JP | 51-40390 | 4/1976 |
| JP | 61-21985 | 1/1986 |
| JP | 2-44771 | 2/1990 |
| JP | 4-354541 | 12/1992 |
| JP | 5-64743 | 3/1993 |
| JP | 6-170233 A | 6/1994 |
| JP | 10-146529 | 6/1998 |
| JP | 3905948 | 1/2007 |
| JP | 2007-530266 A | 11/2007 |
| JP | 2008-512236 A | 4/2008 |

OTHER PUBLICATIONS

David R. Lide et al., "CRC Handbook of Chemistry and Physics," CRC Press, Inc. 75$^{th}$ Edition, 1994-1995, p. 1-15.
International Preliminary Report on Patentability dated Mar. 17, 2011 issued in International Application No. PCT/JP2009/061560.
International Search Report dated Oct. 6, 2009 issued in International Application No. PCT/JP2009/061560.
Masayuki Horio et al., "Fluidized Bed Handbook," Association of Powder Process Industry & Engineering, Japan, pp. 16 & 42, Mar. 25, 1999.
"Miniature Version of Comprehensive Dictionary of Chemistry," Kyoritsu Shuppan Co., Ltd., 39$^{th}$ printing, p. 1014, Jun. 15, 2006.
Supplementary European Search Report for EP Application No. 09804825.9-1270 dated Mar. 12, 2012.

* cited by examiner

*Primary Examiner* — Elizabeth Wood
(74) *Attorney, Agent, or Firm* — Finnegan, Henderson, Farabow, Garrett & Dunner, LLP

(57) ABSTRACT

The present invention provides a zeolite-containing catalyst having excellent shape, fluidity and mechanical strength as a catalyst for a fluidized bed reaction. The present invention provides a zeolite-containing catalyst which is a particulate catalyst containing zeolite and silica, wherein the catalyst has an average particle diameter of 20 to 300 μm and the ratio of the void area in the cross-section of the particle is 30% or less relative to the cross-section area of the particle.

6 Claims, 19 Drawing Sheets

US 9,643,167 B2

ZEOLITE-CONTAINING CATALYST AND METHOD FOR PRODUCING THE SAME, AND METHOD FOR PRODUCING PROPYLENE

This is a division of application Ser. No. 12/995,803, 371(c) date of Dec. 2, 2010, which is the National Stage of PCT/JP2009/061560, filed Jun. 25, 2009, and claims benefit to JP 2008-202806, filed Aug. 6, 2008, all of which are incorporated herein by reference.

TECHNICAL FIELD

The present invention relates to a zeolite-containing catalyst containing zeolite and silica and its production method, and to a production method of propylene using the zeolite-containing catalyst.

BACKGROUND ART

In a fluidized bed reaction, in general, a reactive gas is supplied from a lower part of a reactor filled with a catalyst and catalyst particles are fluidized by the gas flow in the reactor, and then the catalyst particles are contacted with the reactive gas to allow the reaction to proceed. Here, the catalyst used for the fluidized bed reaction is required to have physical properties suitable for the fluidized bed reaction such as chemical performance, particle shape, size, distribution, fluidity and strength.

There is described a suitable property of catalyst particles for achieving a preferable fluidized state in the fluidized bed reaction step, for example, in page 16 of "Fluidized Bed Handbook" (edited by the Association of Powder Process Industry & Engineering, Japan, and published by Baifukan on Mar. 25, 1999). The document describes: "A sufficiently fast mass transfer between gas bubbles and an emulsion phase containing a catalyst is preferable in improving the reaction rate and selection rate. For this purpose, smaller gas bubbles are preferable and it is considered to be preferable that the particles are small and have a smooth and slippery surface. And, it is generally said that preferred particles have a bulk density of 0.6 to 1.0 g·cm$^{-3}$ and an average diameter of 60 to 80 μm." In addition, if there occurs attrition or fracture of catalyst particles due to collision or contact between catalyst particles, between catalyst particles and the reactor, and between the catalyst particles and the reactive gas, accompanied by the fluidization of the catalyst, the fluidity of catalyst particles is decreased and fractured particles are scattered. Consequently, as the property of the fluidized bed reaction catalyst, mechanical strength sufficiently enough to withstand attrition or fracture is also demanded.

That is, a catalyst used for a fluidized bed reaction is required to have a shape, a particle size distribution and the like excellent in fluidity, and mechanical strength (attrition resistance) to withstand collision or contact between catalyst particles, between catalyst particles and the reactor, and between the catalyst particles and the reactive gas.

In order that the catalyst has mechanical strength suitable for the fluidized bed reaction, there is known a method in which a catalyst active component such as zeolite is molded with a support component which becomes a binder such as alumina, silica and clay, and the molded product is calcined. For example, in Patent Document 1, there is described a method in which a buffered silica sol is prepared by adding sulfuric acid and aluminum sulfate to sodium silicate, and to the buffered silica sol are added clay and zeolite to prepare a raw material slurry which is adjusted to a specific pH, followed by spray drying the slurry to produce a hydrocarbon conversion catalyst having high attrition resistance. In addition, in Patent Document 2, there is disclosed a production method of a fluidized catalytic cracking catalyst in which the catalyst is a fluidized bed catalyst with meso-porosity comprising zeolite, gibbsite (aluminum hydroxide), a rare earth metal and a silica matrix, and the silica matrix is prepared from a silica sol prepared by an ion exchange method or from an acidic silica sol containing sodium silicate, sulfuric acid and aluminum sulfate.

[Patent Document 1] Japanese Patent Application Laid-Open No. 51-40390

[Patent Document 2] Japanese Patent Application Laid-Open No. 10-146529

SUMMARY OF THE INVENTION

Problems to be Solved by the Invention

According to the findings of the present inventors, the mechanical strength of a zeolite-based catalyst has a correlation with the surface shape, and a zeolite-based catalyst having a smoother surface shape tends to have higher mechanical strength. In addition, a zeolite-based catalyst having a particle shape nearer to a sphere is preferable from the viewpoint of mechanical strength, and a catalyst having no sufficient mechanical strength has a higher tendency of having a shape in which gases and the like incorporated are blown out from a part of the sphere.

On the other hand, the present inventors conducted a follow-up study on the catalyst preparation methods described in Japanese Patent Laid-Open No. 51-40390 and Japanese Patent Laid-Open No. 10-146529. The results showed that significant unevenness was observed on the surfaces of both the catalysts obtained by the methods described in these documents and both the catalysts had a shape far from a smooth sphere.

In light of the above circumstances, an object of the present invention is to provide a zeolite-containing catalyst having excellent shape, fluidity and mechanical strength as a catalyst for a fluidized bed reaction and a method for producing the catalyst, and a method for the production of propylene using the zeolite-containing catalyst.

Means for Solving the Problems

As a result of earnest studies to solve the above-described problems, the present inventors have found that there may be produced a zeolite-containing catalyst having excellent mechanical strength by decreasing the void content inside the catalyst, and have completed the present invention.

That is, the present invention is as follows:

[1] A zeolite-containing catalyst which is a particulate catalyst containing zeolite and silica, wherein the catalyst has an average particle diameter of 20 to 300 μm and the ratio of the void area in the cross-section of said particle is 30% or less relative to the cross-section area of the particle.

[2] The zeolite-containing catalyst according to [1], wherein said zeolite is an MFI-type zeolite.

[3] The zeolite-containing catalyst according to [1] or [2], wherein the content rate of said zeolite is from 10 to 90% by mass, the content rate of said silica is from 10 to 90% by mass, and the total content rate of said zeolite and said silica is 50% by mass or more.

[4] A method for producing a zeolite-containing catalyst according to any one of [1] to [3], comprising: the steps of obtaining a dried powder by spray drying a raw material mixture containing zeolite and colloidal silica; and calcining said dried powder, wherein said raw material mixture contains at least one water-soluble compound selected from the group consisting of a nitrate salt, an acetate salt, a carbonate salt, a sulfate salt and a chloride in a mass ratio of 0.01 to 5.0 relative to the silica contained in said colloidal silica.

[5] The method for producing a zeolite-containing catalyst according to [4], wherein the ratio of the mass of said colloidal silica to the total amount of silica contained in said raw material mixture is 50% by mass or more.

[6] The method for producing a zeolite-containing catalyst according to [4] or [5], wherein said raw material mixture is acidic.

[7] The method for producing a zeolite-containing catalyst according to any one of [4] to [6], wherein said water-soluble compound is at least one selected from the group consisting of ammonium nitrate, ammonium acetate, ammonium carbonate, ammonium sulfate and ammonium chloride.

[8] A method for producing propylene comprising the step of contacting a zeolite-containing catalyst according to any one of [1] to [3] with a hydrocarbon and/or an alcohol in a fluidized bed reactor.

Effect of the Invention

The present invention can provide a zeolite-containing catalyst having excellent shape, fluidity and mechanical strength as a catalyst for a fluidized bed reaction and a method for producing the catalyst, and a method for the production of propylene using the zeolite-containing catalyst.

BEST MODE FOR CARRYING OUT THE INVENTION

Figure 1:
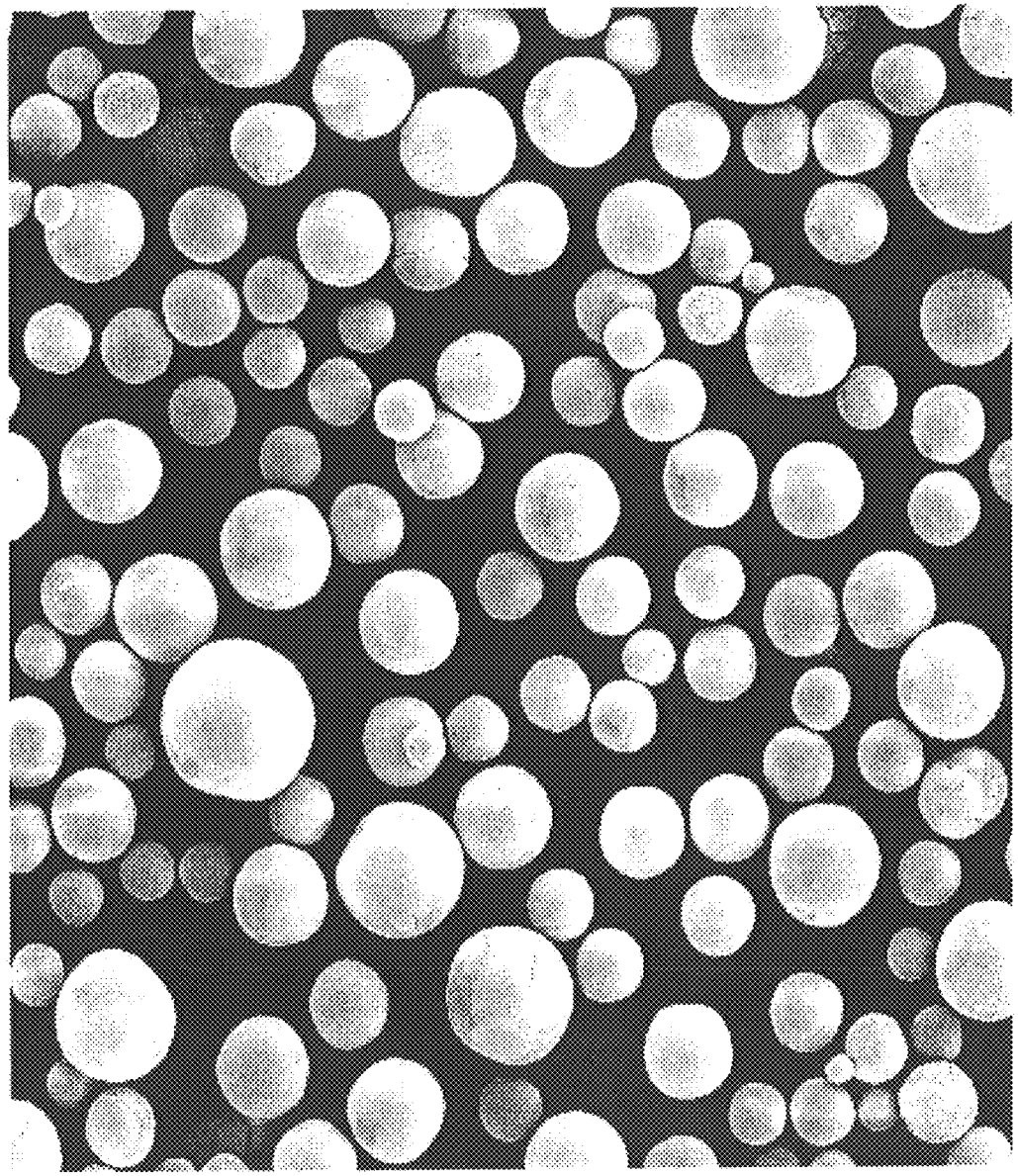
FIG. 1 is an electron microscope photograph (at a magnification of 150 times) showing a zeolite-containing catalyst of Example 1.

Hereinafter, there will be described embodiments (hereinafter, referred to as "the present embodiment") for carrying out the present invention in detail. In addition, the present invention is not limited to the following embodiments, and various modifications may be made within the gist of the present invention.

Further, the term "silica" as used herein refers to silica which is contained in a silica raw material used for the production of a zeolite-containing catalyst, and unless otherwise specified, it does not mean the silica constituting zeolite.

[Zeolite-Containing Catalyst]

The zeolite-containing catalyst of the present invention is a particulate catalyst containing zeolite and silica, in which the particle has an average particle diameter of 20 to 300 μm and the ratio of the void area in the cross-section of the particle is 30% or less relative to the cross-section area of the particle.

The term "zeolite" as used herein refers to a crystalline porous aluminosilicate or a metallosilicate (zeolite in which a part or all of the aluminum atoms constituting the skeleton of a crystalline porous aluminosilicate is substituted with a substitutable element such as Ga, Fe, B, Cr and Ti), and includes a phosphate-based porous crystal having a structure similar to or same as that of the aluminosilicate and metallosilicate.

Specifically, a zeolite having a small pore diameter (structure of oxygen 8-membered ring or less) includes chabazite (CHA: a framework type code name specified by International Zeolite Association, the same shall apply hereinafter), erionite (ERI) and A type (LHA). A zeolite having intermediate diameter (structure of oxygen 10-membered ring) includes ferierite (FER), ZMS-11 (MEL), ZSM-5 (MFI) and AlPO$_4$-11 (AEL). In addition, a zeolite having a large pore diameter (structure of oxygen 12-membered ring) includes X type (FAU), Y type (FAU), faujasite (FAU), β type (BEA), mordenite (MOR), ZSM-12 (MTW) and ALPO$_4$-5 (AFI). Further, a zeolite having an ultralarge pore diameter (structure of oxygen 14-membered ring or more) includes UTD-1 (DON), CIT-5 (CFI) and VPI-5 (VFI).

Among these, preferred is a zeolite having an intermediate pore diameter composed of oxygen 10-membered ring, more preferred is an MFI-type zeolite and especially preferred is ZSM-5. When a catalyst containing a zeolite having such an intermediate pore diameter is used for a conversion reaction of hydrocarbon which is conducted in a gas phase such as a fluid catalytic cracking (FCC) reaction, the coke content generated with the reaction tends to be small compared to the case where a zeolite having a large pore diameter is used. Accordingly, since pore occlusion due to the coke is unlikely to occur and the catalyst lifetime may be extended, preferred is the zeolite having an intermediate pore diameter. In addition, the zeolite having an intermediate pore diameter is preferable because the reacting molecules of an alcohol or a hydrocarbon or the like easily penetrate into pores and the active sites on the catalyst may be effectively used, compared to the zeolite having a small pore diameter. Further, the zeolite having a small pore diameter has a greater tendency of decreasing the activity by the coke generated with the reaction than the zeolite having an intermediate pore diameter.

Among the zeolites having an intermediate pore diameter, especially preferred is a zeolite (MFI-type zeolite; especially ZSM-5) having an MFI-type structure because it has a high heat resistance and a characteristic catalytic activity due to the shape selectivity and strong solid acidity.

The cation-type zeolite may be H$^+$ type and may be one in which a part or all of H$^+$ is substituted with a metal cation.

Especially, when the zeolite-containing catalyst of the present embodiment is used as a fluidized bed reaction catalyst in producing propylene by contacting with a hydrocarbon containing ethylene, the zeolite-containing catalyst preferably contains at least one metal selected from the group consisting of metals belonging to Group IB in the Periodic Table, that is, copper, silver and gold. The metal incorporated in the zeolite-containing catalyst is preferably copper and/or silver, and is especially preferably silver. In addition, in the present specification, the "Periodic Table" refers to the periodic table described in Page 1 to 15, CRC Handbook of Chemistry and Physics, 75th edition, edited by David R. Lide, et al., published by CRC Press Inc. (1994 to 1995).

The metal incorporated in the zeolite-containing catalyst is contained in the zeolite in the catalyst in the corresponding cation state or is supported on a catalyst.

In addition, a zeolite modified with a phosphor compound is also preferably used. The phosphorus compound includes phosphoric acid, phosphorous acid, hypophosphorous acid, pyrophosphoric acid, polyphosphoric acid, ammonium monohydrogen phosphate, ammonium dihydrogen phosphate, ammonium phosphate and aluminum phosphate. There may be used a catalyst obtained by absorbing or impregnating these compounds in an amount of 0.1 to 5% by mass in the zeolite as a phosphorus element.

The zeolite-containing catalyst of the present embodiment has an average particle diameter in the range of 20 to 300 μm. The average particle diameter is preferably from 20 to 200 μm, more preferably from 40 to 100 μm, further more preferably from 40 to 80 μm and especially preferably from 40 to 60 μm.

In addition, from the viewpoint of fluidity, the zeolite-containing catalyst of the present embodiment preferably has a particle size distribution such that the particle diameters of 80% or more particles in the whole particles are in the range from 2 to 0.2 times the average particle diameter.

The terms "particle diameter" and "particle size distribution" as used herein mean a value measured by a laser diffraction/scattering type particle size analyzer. In addition, the term "average particle diameter" as used herein means a cumulative average diameter which is a value obtained by measuring the particle size distribution (ratio of particles present in a fixed particle size range) of a powdery zeolite-containing catalyst by the above analyzer and determining the cumulative particle size distribution by defining the whole volume as 100%. The point where the cumulative is 50% is a particle diameter, that is, a cumulative average diameter (a center diameter, a median diameter).

From the viewpoint of fluidity and strength, the zeolite-containing catalyst of the present embodiment preferably is spherical. As shown in FIGS. 10 to 17 described later in detail, the conventional zeolite-containing catalyst is far from a spherical shape because it frequently has a shape in which a hole formed in the vicinity of the center is ruptured or the particle surface has significant unevenness. The term "spherical shape" as used herein as a catalyst shape is not always required to be a true sphere or a nearly true sphere because the purpose is to compare it with such a conventional catalyst shape, and means to a degree that the catalyst of the present embodiment is not in a ruptured shape and has no significant protrusions or dents. However, needless to say, it is more preferable that the shape of the zeolite-containing catalyst is apparently near a true sphere. A spherical zeolite-containing catalyst is also advantageous in durability because it is smoothly fluidized in a fluidized bed reactor and tends to exhibit large strength.

If the zeolite-containing catalyst has an average particle diameter of less than 20 μm, the angle of repose, which is a measure of fluidity of a catalyst, tends to increase, and when used as a fluidized bed reaction catalyst, the fluidity of the catalyst is deteriorated. If the zeolite-containing catalyst has an average particle diameter exceeding 300 μm, the mechanical strength of the catalyst tends to decrease, and when used as a fluidized bed reaction catalyst, the central portion of the catalyst particles tends not to be effectively used for the reaction.

The zeolite-containing catalyst of the present embodiment has a structure in which the ratio of the void area in the cross-section of the particle is 30% or less relative to the cross-section area of the particle. The ratio of the void area is preferably 20% or less, more preferably 15% or less and especially preferably 10% or less.

The term "the ratio of the void area in the cross-section of the particle" as used herein means a value measured as follows.

That is, firstly, the particles of the zeolite-containing catalyst are embedded with a resin, followed by grinding it to scrape away the cross-section of the catalyst particles. The cross-section is observed by an electron microscope equipped with an image analysis device and the cross-section area of one particle and the area of the void portion in the cross-section of the particle are measured at a magnification of 800 to 2000 times. Here, in case of a catalyst having a hole as in the above conventional example, "the cross-section area" is defined as a value including the area of the void portion. In addition, in case of the particle having a shape in which a hole is ruptured, both ends of portions (opening portion) in which a part of the circumference is cut by "rapture" are connected with a straight line so as to occlude the opening portion, and the area in the range surrounded by the straight line and the outer circumference is defined as the cross-section area. For example, in case of the catalyst shown in FIG. 11, the substantial portion is a C-character type, but the area of the whole range surrounded by the straight line connecting the opening portion and the substantial portion of the C-character type is defined as the cross-section area (the cross-section area includes the area of the opening portion observed black in the vicinity of the center in the figure). The area of the void portion in this example is defined as the area in the portion surrounded by the straight line connecting the opening portion and the inner wall of the substantial portion of the C-character type.

Subsequently, the ratio of the area of the void portion to the cross-section area of particles is calculated. Then, a series of operations are carried out for 100 particles and the arithmetic average (arithmetical mean) value is defined as the ratio of the void area in the cross section of the particle. However, in order to measure the cross section in the vicinity of the center of the particle, particles having a diameter in the range of ±10% of the average particle diameter are selected as 100 particles to be measured.

If the ratio of the void area exceeds 30%, the mechanical strength of the particle tends to decrease.

As described above, the conventional zeolite-containing catalyst had a shape in which a large hole is formed in the vicinity of the center, or a hole is ruptured, or the particle surface has significant unevenness. Until now, there has never been found out a zeolite-containing catalyst, which has a sophisticated structure in which the void portion inside the particle is extremely small and thus is extremely high in mechanical strength, as with the zeolite-containing catalyst of the present invention. If a catalyst used for a fluidized bed reaction has high mechanical strength, it is extremely important for an industrial process because powderization of the catalyst is unlikely to occur even during the long period of use and a suitable fluidized state may be stably maintained.

As described above, since a zeolite-containing catalyst having high mechanical strength exhibits a tendency that it is not easily abraded, the mechanical strength of the catalyst depends on the attrition loss of the catalyst. The attrition loss for a fixed period time is measured by using a jet fluidic apparatus. The attrition loss is preferably 3% by mass or less, more preferably 2% by mass or less and especially preferably 1% by mass or less.

The zeolite-containing catalyst of the present embodiment has an angle of repose of preferably 25 to 30° and more preferably from 25 to 28°. If the angle of repose is 30° or less, the fluidity of the catalyst is more preferable. The angle of repose is measured by the method described in Example described later.

Regarding the composition of the zeolite-containing catalyst of the present embodiment, in a shape after calcining, preferably, (I) the content rate of the zeolite is from 10 to 90% by mass, (II) the content rate of the silica is from 10 to 90% by mass, and (III) the total content rate of the zeolite and silica is 50% by mass or more with respect to the total content of the zeolite-containing catalyst. More preferably, (I) the content rate of the zeolite is from 20 to 60% by mass, (II) the content rate of the silica is from 80 to 40% by mass, and (III) the total content rate of the zeolite and silica is 70% by mass or more. Much more preferably, (I) the content rate of the zeolite is from 30 to 50% by mass, (II) the content rate of the silica is from 70 to 50% by mass, and (III) the total content rate of the zeolite and silica is 90% by mass or more.

(I) If the content rate of the zeolite is less than 10% by mass, the activity per unit amount of catalyst becomes low and the required amount of the catalyst tends to increase in order to obtain a desired activity because the content of the zeolite which is an active component is small. If the content rate of the zeolite exceeds 90% by mass, the mechanical strength of catalyst particles tends to decrease because the zeolite itself does not have preferable adhesiveness.

(II) If the content rate of the silica is less than 10% by mass, the mechanical strength of catalyst particles tends to decrease for the same reason as above. If the content rate of the silica exceeds 90% by mass, the activity per unit amount of catalyst becomes low and the required amount of the catalyst tends to increase in order to obtain a desired activity for the same reason as above.

(III) If the total content rate of the zeolite and silica is less than 50% by mass, the activity per unit amount of catalyst becomes low and the required amount of the catalyst tends to increase in order to obtain a desired activity for the same reason as above, and the mechanical strength of catalyst particles tends to decrease.

Since the zeolite-containing catalyst of the present embodiment has a specific average particle diameter and the ratio of the void area in the cross-section of the particle is 30% or less relative to the cross-section area of the particle, it has high fluidity and mechanical strength. For this reason, it is especially preferable as a catalyst for a fluidized bed reaction.

[Method for Production of Zeolite-Containing Catalyst]

The method for the production of the zeolite-containing catalyst of the present embodiment is a method for obtaining a zeolite-containing catalyst which has an average particle diameter of 20 to 300 µm and in which the ratio of the void area in the cross-section of the particle is 30% or less relative to the cross-section area of the particle. In order to obtain such a zeolite-containing catalyst, various conditions as described below in detail need only to be adjusted. The method for the production of the zeolite-containing catalyst of the present embodiment preferably comprises: (ii) a step of obtaining dried powders by spray drying a raw material mixture containing zeolite and a colloidal silica; and (iii) a step of calcining the dried powders. The method for the production of the zeolite-containing catalyst may comprise: prior to the above step (ii), (i) a step of preparing the raw material mixture containing zeolite and a colloidal silica; and/or after the step (iii), (iv) a step of ion-exchanging calcined powders obtained by calcining.

[Step (i): Preparation Step of Raw Material Mixture]

The step (i) is a step of preparing a raw material mixture (hereinafter, also referred to as a "raw material slurry") containing zeolite, a colloidal silica and at least one water-soluble compound selected from the group consisting of a nitrate salt, an acetate salt, a carbonate salt, a sulfate salt and a chloride.

The molar ratio $SiO_2/Al_2O_3$ (silica/alumina ratio) of the zeolite is preferably from 15 to 1000 and more preferably from 20 to 300. In addition, when zeolite is a metallosilicate, the molar ratio $SiO_2/Al_2O_3$ (silica/alumina ratio) is calculated by assuming the number of moles of alumina containing an aluminum atom substituted with a substitutable element such as Ga, Fe, B, Cr and Ti as the number of moles of alumina present in the metallosilicate.

The raw material zeolite is preferably in a state in which primary particles of the zeolite are dispersed. In general, zeolite frequently forms a secondary agglomeration because primary particles of the zeolite having a diameter of approximately 0.05 to 10 μm are partly bonded together. When the zeolite which remains to form a secondary agglomeration is molded with a binder such as silica, the surface of the molded particles becomes rough and mechanical strength tends to decrease because a void portion is likely to be formed inside the particle. For this reason, if the zeolite forms a secondary agglomeration, it is preferable that the zeolite is used by mechanically pulverizing using a jet mill or the like to deagglomerate. As the pulverizing method of zeolite, it is more preferable to use a method of using a jet mill in which the pulverizing treatment is performed by jetting compressed air at ultrahigh speed than to use a conventional ball mill. On this occasion, it is especially preferable that zeolite is deagglomerated until the average particle diameter of the zeolite becomes in the range of 0.05 to 5 μm.

In addition, the agglomeration state of the zeolite can be observed by an electron microscope. Further, the average particle diameter of the zeolite is measured by a laser diffraction/scattering type particle size analyzer in the same manner as above.

The colloidal silica used for a catalyst raw material is preferably prepared by an ion-exchange method.

In general, water glass (sodium silicate) is frequently used as a raw material for the production of a fluidized bed catalyst. However, the results of studies of the present inventors showed that when water glass is used as a main component of a binder silica, not only the shape of a particle surface of a catalyst tends to be deteriorated but also there is a problem with respect to catalyst performance. That is, if sodium silicate is used as a raw material of the binder silica, sodium, which is a catalyst poison for a solid acid catalyst, is contained in a large amount in a catalyst. Although it is possible to reduce the concentration of sodium contained in a binder, in order to remove sodium from the catalyst to a low concentration where the catalyst reaction is not adversely affected, there are required extremely complicated operations such as plural times of hot water washing and ion-exchanging using a special device for preventing the breakage of particles.

On the other hand, when a colloidal silica prepared by an ion-exchange method is used as a main component, the surface of a catalyst particle becomes smooth. As used herein, "the surface (of a particle) is smooth" refers to that the surface of the particle apparently has no unevenness when observation is carried out by a microscope photograph at a magnification of 150 times. In addition, when the colloidal silica is used as a main component, since the sodium content contained in the raw material is small, the ion-exchanging step is not always required and sodium may be removed by a convenient operation.

However, when the colloidal silica is simply used instead of water glass in the conventional technique, there is a problem that a large hole is formed at the center of a catalyst molded by spray drying and the catalyst particles become brittle. On the other hand, in the present embodiment, the problem has been solved by allowing a predetermined amount of the water-soluble compound described later to coexist with a catalyst raw material.

The larger the ratio of the silica (derived from the colloidal silica) obtained by using the colloidal silica as a raw material to the total amount of the silica (excluding the silica constituting zeolite) contained in the zeolite-containing catalyst, the more preferable. Specifically, the ratio is preferably 50% by mass or more, more preferably 60% by mass or more, further more preferably 70% by mass or more, still further more preferably 80% by mass or more and especially preferably 90% by mass or more.

Similarly, the ratio of the colloidal silica to the total amount of the silica (excluding the silica constituting zeolite) contained in the raw material mixture is preferably 50% by mass or more, more preferably 60% by mass or more, further more preferably 70% by mass or more, especially preferably 80% by mass or more and extremely preferably 90% by mass or more. In addition, for example, when the silica source contained in the raw material mixture is water glass and the colloidal silica, the ratio of the colloidal silica to the total amount of the silica contained in the raw material mixture means the ratio (the silica contained by the colloidal silica)/(the silica contained by the colloidal silica+the silica contained by the water glass) on a mass basis. As the ratio of the colloidal silica contained in the raw material mixture is higher, the surface of the resulting catalyst tends to become smoother. Especially if the ratio is 70% by mass or higher, there are less particles having protrusions or depressions on the surface (40% or less), even when observation is carried out at a magnification of 1600 times or more. In addition, "protrusions or depressions" show a state where local unevenness is generated on the surface and are different from a state where linear cracks are formed on the surface.

As the colloidal silica prepared by an ion-exchange method, a commercially available one may be used. A colloidal silica stabilized by ammonia or amine is especially preferable in that the content of an alkali metal is small. The smaller the content (by mass) of an alkali metal in the colloidal silica, the more preferable, and the content is preferably 1000 ppm or less and more preferably 250 ppm or less as an alkali metal. The alkali metal contained in the zeolite-containing catalyst may be reduced by using a colloidal silica having a small content of an alkali metal as a main component of silica. The content of an alkali metal with respect to the total mass of the zeolite-containing catalyst is preferably 5000 ppm or less, more preferably from 10 to 3000 ppm, further more preferably from 10 to 1000 ppm, still further more preferably from 10 to 300 ppm and especially preferably from 10 to 100 ppm. If the content of an alkali metal exceeds 5000 ppm, the catalytic activity tends to decrease. On the other hand, if the content of an alkali metal is less than 10 ppm, there is no useful effect on catalytic activity. If a plurality of alkali metals is contained in the zeolite-containing catalyst, the total content of each alkali metal is preferably in the above range.

In order to measure the content of the alkali metal contained in the zeolite-containing catalyst, firstly, the catalyst is dissolved in royal water at 210° C. using a microwave (produced by Milestone Inc., Type: ETOS PLUS) and a small amount of residue is filtered. Thereafter, the amount of the alkali metal in the filtrate is measured by a conventional method using an ICP emission spectroscopy. The content of the alkali metal in the zeolite-containing catalyst may be derived from the content of the alkali metal contained in the filtrate. The measurement conditions of the ICP emission analysis may be set at a high frequency power of 1 kw, a plasma gas flow rate of 13 L/min, a sheath gas flow rate of 0.15 L/min and a nebulizer gas flow rate of 0.25 L/min.

The silica contained in the colloidal silica has an average particle diameter of preferably from 3 to 50 nm and more preferably from 4 to 25 nm. If the silica in the colloidal silica has an average particle diameter of 50 nm or less, the mechanical strength of molded particles tends to further increase. The average particle diameter of silica is measured by a laser-type dynamic light-scattering particle size distribution analyzer.

To the raw material slurry is added at least one water-soluble compound selected from the group consisting of a nitrate salt, an acetate salt, a carbonate salt, a sulfate salt and a chloride.

As described in Page 1014 of Miniature Version of Comprehensive Dictionary of Chemistry, 39th printing (published by Kyoritsu Shuppan Co., Ltd., on Jun. 15, 2006), the term "salt" as used herein refers to a compound generated by the neutralization reaction of an acid and a base, which is composed of the negative component of the acid and the positive component of the base.

In addition, the term "water-soluble compound" as used here means a compound having a solubility of 1 g or more in 100 g of water at 25° C. The water-soluble compound preferably is a compound having a solubility of 10 g or more in 100 g of water at 25° C., and for example, includes an ammonium salt, an aluminum salt and a sodium salt.

A more preferred water-soluble compound is an ammonium salt which is high in water-solubility and may be decomposed and removed from a catalyst in the calcining step described later. More specifically, it is more preferable that the water-soluble compound is one or more ammonium salts selected from the group consisting of ammonium nitrate, ammonium acetate, ammonium carbonate, ammonium sulfate and ammonium chloride, and most preferred is ammonium nitrate.

The addition amount of the water-soluble compound in the raw material slurry is in the range of 0.01 to 5.0 at a mass ratio to the silica contained in the colloidal silica (hereinafter, described as "the ratio of the water-soluble compound to the colloidal silica"). The addition amount of the water-soluble compound is in the range of more preferably from 0.03 to 3.0, further more preferably from 0.05 to 2.0, especially preferably from 0.1 to 1.0 and extremely preferably from 0.25 to 0.5. If the addition amount of the water-soluble compound is 0.01 or less at a mass ratio to the silica obtained by using the colloidal silica as a raw material, the ratio of the void area of the particle cross-section becomes large and the mechanical strength of the particle tends to decrease. If the addition amount of the water-soluble compound is 5.0 or more at a mass ratio to the silica, when the water-soluble compound added is decomposed during the calcining of the catalyst described later, the decomposed amount is large. Therefore, excessive pores are formed inside the particle and the mechanical strength of the particle tends to decrease. In addition, the drying property of droplets is deteriorated during the spray drying described later and the adherence of the raw material slurry to the inside of the spray dryer tends to increase.

The raw material slurry is preferably acidic. The pH of the raw material slurry is preferably from 0.01 to 3.0, more preferably from 0.1 to 2.0 and especially preferably from 0.5 to 1.5. This is for preventing that the colloidal silica is unstabilized and gelated when the water-soluble compound and the colloidal silica coexist in the raw material slurry. A particle having high mechanical strength may be obtained by preventing the gelation of the colloidal silica and spray drying it while maintaining the sol state.

In order to form a raw material slurry without gelation of the colloidal silica, the addition and mixing of each raw material component in preparing the raw material slurry are preferably carried out by the following methods a) and b).

a) A method of preparing an acidic raw material slurry in which the pH of the slurry obtained by adding the colloidal silica to zeolite is preliminarily adjusted to acidity by adding an acid such as nitric acid, sulfuric acid and hydrochloric acid and followed by adding a water-soluble compound.

b) A method of preparing an acidic raw material slurry in which the pH of the colloidal silica is preliminarily adjusted to acidity by adding an acid such as nitric acid, sulfuric acid and hydrochloric acid and followed by adding a water-soluble compound and then adding zeolite.

The solid content concentration of the raw material slurry after adding zeolite, a colloidal silica, a water-soluble compound and the like is preferably from 5 to 60% by mass and more preferably from 15 to 40% by mass. In order to adjust the solid content concentration, water may be arbitrarily added to the raw material slurry. Here, the solid content concentration of the raw material slurry is a ratio of the mass of the residue obtained by drying the raw material slurry at 100° C. to the total mass of the raw material slurry. The temperature during the preparation of the raw material slurry is preferably from 5 to 95° C., more preferably from 10 to 70° C. and especially preferably from 10 to 40° C.

When stirring the raw material slurry, the stirring power and stirring time are selected such that individual raw material components are sufficiently mixed together. The stirring time is preferably from 0.5 to 48 hours and more preferably from 1 to 5 hours.

For the purpose of adjusting the mechanical strength, bulk density, shape, catalytic performance and the like of the catalyst particles, the raw material slurry may contain a clay mineral such as kaolin, diatomaceous earth, alumina, titania, zirconia, ceria and the like. These may be added to the raw material slurry in a powder, solution or sol state. In addition, for the purpose of making the shape of the catalyst particles near a true sphere, a surfactant for adjusting the surface tension of the raw material slurry may be added to the raw material slurry.

[Step (ii): Drying Step]

The step (ii) is a step of spray drying the raw material slurry obtained in the above step (i) to obtain dried powders. It is a preferable method that the spray drying is carried out using a spray dryer which is industrially used. The spraying method of the raw material slurry may be carried out by a rotating disk method, a two-fluid nozzle method and a high-pressure nozzle method and the like. Among these, an especially preferable spraying method is a rotating disk method. The spray drying may be carried out by spraying the raw material slurry together with a fluid such as air heated by steam and an electric heater, or an inert gas such as nitrogen and helium.

The fluid temperature at a spray dryer inlet is preferably from 100 to 400° C. and more preferably from 150 to 300° C. The fluid temperature at a spray dryer outlet is preferably from 80 to 200° C. and more preferably from 90 to 150° C.

Regarding the spray drying conditions such as the disk rotation number in the rotating disk method, the spray gas amount in the nozzle method, the feed amount of the raw material slurry, the feeding amount of the heated fluid, and the ratio of these feeding amounts, they may be arbitrarily adjusted so that the adherence of the raw material slurry to the inside the spray dryer is small and the catalyst particles in a state after calcining have an average particle diameter in the range of 20 to 300 μm.

[Step (iii): Calcination Step]

The step (iii) is a step of obtaining calcined particles by calcining the dried powders obtained in the above step (ii). The calcination of the dried powders may be carried out by using a muffle furnace, a rotating furnace, a tunnel furnace, a tubular furnace, a fluidized calcination furnace, a kiln furnace and the like. An industrially preferable method is one in which calcination is carried out using a continuous feed-type rotary kiln furnace. From the viewpoint of improving the strength of the catalyst particles, the calcination temperature is preferably from 400 to 1000° C. and more preferably from 500 to 800° C. From the viewpoint of the strength of the catalyst particles, the calcination time is preferably from 0.1 to 48 hours, more preferably from 0.5 to 24 hours and further more preferably from 1 to 10 hours. The calcination of the dried powders is preferably carried, out under an atmosphere of air, water vapor, or an inert gas such as nitrogen and helium. In addition, the calcination may be carried out under increased pressure or under reduced pressure. The calcination may be carried out repeatedly.

In the calcination step, a part or all of the nitrate salt, acetate salt, carbonate salt, sulfate salt and chloride, which are added as a raw material component, may be removed from the dried powders. In addition, the dried powders are calcined to sinter silica, thereby enabling dramatically increasing the mechanical strength of the catalyst particles.

[Step (iv): Ion-Exchange Step]

The step (iv) is an ion-exchange step in which an alkali metal component in the calcined powders is removed by contacting the calcined powders obtaining in the above step (iii) preferably with a mineral acid and/or a (metal) cation-containing solution, and a cation on the zeolite is converted into $H^+$ or a desired metal cation.

The ion exchange method in the ion-exchange step may be similar to that of the conventional zeolite-containing catalyst. As the ion-exchange method, for example, it is carried out by contacting a mineral acid aqueous solution such as 0.1 to 3 mol concentration of nitric acid, sulfuric acid and hydrochloric acid and/or a (metal) cation-containing aqueous solution such as an ammonium nitrate aqueous solution with the calcined powders at 10 to 95° C. for 0.1 to 48 hours. Thereafter, the resulting powders are washed with water and dried, followed by again calcining at 500 to 600° C., if needed.

The production method of the zeolite-containing catalyst of the present embodiment preferably also has a step in which the calcined powders or powders passed through the ion-exchanging step are contacted with a gas containing steam at 500 to 700° C. and then subjected to steaming treatment. In the zeolite-containing catalyst obtained by the steaming treatment, the acid property of zeolite is controlled and the deterioration caused by the formation of a carbonaceous material (coking) during the reaction is suppressed. In addition, if the zeolite-containing catalyst is used, the yield of the target substance may be increased.

The zeolite-containing catalyst of the present embodiment may be calcined powders obtained by the above calcination step, or powders obtained by the above ion-exchange step, or powders obtained by the above step of steaming treatment.

In addition, there are described (ii) spray drying, (iii) calcination step and (iv) ion-exchange step as mentioned above. However, from the viewpoint of reducing the sodium content of the resulting zeolite-containing catalyst, if the silica raw material contains water glass, the spray-dried powders are preferably ion-exchanged before calcination. If the spray-dried powders are ion-exchanged after the calcination step, it tends to be difficult to remove the sodium contained in the calcined product.

The production method of the above zeolite-containing catalyst of the present embodiment may be applied not only to the production of a catalyst for a fluidized bed reaction, but to the production of a catalyst for a fixed bed reaction.

The catalyst for the fixed bed reaction is generally used in a state where an active component such as zeolite is molded with a binder such as silica into a sphere, a tablet, a cylindrical shape, a ring shape, a honeycomb shape and the like having a diameter of approximately from 1 mm to a few mm. In this case, if the production method of the above zeolite-containing catalyst is applied after appropriate modification, there may be produced a catalyst for the fixed bed reaction having high mechanical strength and less alkali content. If the catalyst has high mechanical strength, it is also important for a fixed bed catalyst. That is, when a catalyst is filled in a reactor, and when a catalyst is used in a reactor for a long period of time, if the catalyst has high mechanical strength, cracking and powderization due to an external stress or a thermal history may be suppressed.

According to the production of the zeolite-containing catalyst of the present embodiment, there may be formed strong catalyst particles for a fluidized bed reaction in which the void portion inside the particle is extremely small, and the filling state of zeolite and silica has a uniform and dense structure. The reason is unclear, but the present inventors presume as follows. However, the reason is not limited to this.

Firstly, in preparing particles having an average particle diameter of 20 to 300 μm by spray drying the raw material slurry, which contains zeolite and a colloidal silica and contains no specific water-soluble compounds relating to the present embodiment, using a well-known method, there occur breakage of particles, and pore opening and depressions on the particle surface due to the mechanism having the following processes 1) to 3).

Process 1) A liquid vaporizes from the surface of the droplets sprayed to start the contraction of the droplets and then the droplet surface is solidified and contracted mainly by bonding together of the silica particles.

Process 2) Thereafter, the liquid continues to vaporize inside the droplets, but a gas generated by the solidification of the droplet surface is confined inside the droplets, thereby increasing the internal pressure of the droplet. As a result, the gas is blown out from the inside and there occur breakage (cracking or chipping) of the particles obtained from the droplet or pore opening and depressions on the particle surface.

Process 3) After spray drying, when the temperature is decreased, the surface of the particles is depressed even if the inside of the particle becomes negative pressure. In the course of these steps, the resulting particles become brittle because many void portions are formed inside the particle.

On the other hand, in case of the production method of the zeolite-containing catalyst of the present embodiment, in the above process 2), since the water-soluble compound added forms a state where it is adsorbed on the silica particle surface of the colloidal silica and enters between particles of the silica particles, the silica particles are not densely bonded together. For this reason, the moisture inside the particle obtained from droplets is not confined but may immediately move from between the silica particles to the outside of the particles and neither pressure increase nor negative pressurization inside the particles occurs. As a result, it is presumed that there is formed a structure in which the pore opening of the particle surface or the void portion inside the particle is extremely little and zeolite and silica are densely and uniformly filled.

[Production Method of Propylene]

The production method of propylene of the present embodiment comprises a step of contacting the zeolite-containing catalyst with a hydrocarbon and/or an alcohol in a fluidized bed reactor. From the viewpoint of producing propylene at a high yield, the hydrocarbon and/or the alcohol which are raw materials preferably have a carbon number in the range of 2 to 12. From the same viewpoint, the hydrocarbon preferably contains an olefin other than propylene.

The hydrocarbon and/or alcohol which are reaction raw materials are not required to be of high quality and may be of industrial grade.

The reaction raw material used for the production method of propylene of the present embodiment contains ethylene in an amount of preferably 20% by mass or more and more preferably 25% by mass or more. In addition, water is preferably fed into a reactor together with the raw material containing ethylene. The feed ratio of water is preferably 1 part by mass or more, more preferably from 5 to 100 parts by mass and further more preferably from 10 to 80 parts by mass, based on 100 parts by mass of the raw material containing ethylene. In addition, in the production method of propylene of the present embodiment, it is a preferred embodiment that propylene is separated from the reaction product and at least a part of low-boiling components containing the remaining ethylene and/or high-boiling components containing butene are recycled by feeding them into the fluidized bed reactor as a raw material.

As the reaction raw material containing ethylene, there may be used one obtained by the thermal cracking, steam cracking or oxidative dehydrogenation reaction of ethane, or one obtained by the dehydration reaction of ethanol. The reaction raw material may contain an olefin and a paraffin. The paraffin includes, for example, methane, ethane, propane, butane, pentane, hexane, heptanes, octane and nonene. In addition, the olefin includes, for example, propylene, butene, pentene, hexene, heptene, octene and nonene. The reaction raw material containing ethylene may contain, in addition to the above compounds, a cycloparaffin such as cyclopentane, methylcyclopentane and cyclohexane; a cycloolefin such as cyclopentene, methylcyclopentene and cyclohexene; a diene such as cyclohexadiene, butadiene, pentadiene and cyclopentadiene; and/or an acetylene such as acetylene and methyl acetylene. Further, the reaction raw material containing ethylene may contain an oxygen-containing compound such as t-butylalcohol, methyl t-butyl ether, diethyl ether, methyl ethyl ether, dimethyl ether, ethanol and methanol. In addition, the reaction raw material containing ethylene may further contain water, hydrogen, nitrogen, carbon dioxide and carbon monoxide.

When the reaction raw material contains ethanol, ethanol (biomass ethanol) obtained from plant resources may be used. Such an ethanol specifically includes ethanol obtained by the fermentation of sugarcane or corn or the like and ethanol obtained from wood resources such as scrap wood, thinned wood, rice straw and agricultural crops.

The reaction temperature in the fluidized bed reaction is preferably from 300 to 650° C., more preferably from 400 to 600° C. The reaction pressure is preferably from 0.1 to 30 atm. and more preferably from 0.5 to 10 atm.

The feed rate of the reaction raw material at a weight hour space velocity (WHSV) on the zeolite-containing catalyst basis is preferably from 0.1 to 20 $hr^{-1}$ and more preferably from 0.5 to 10 $hr^{-1}$.

In the production method of propylene of the present embodiment, when the reaction raw material containing ethylene is used, the conversion rate of ethylene may be controlled by adjusting the above reaction conditions. For example, the reaction conditions are preferably controlled so that the conversion rate of ethylene is in the range of 45 to 85% and more preferably from 50 to 80%.

In the production method of propylene of the present embodiment, if the zeolite-containing catalyst is used for the reaction for a long period as a fluidized bed reaction catalyst, a carbonaceous material (coke) is generated on the catalyst and the catalytic activity may be decreased. In this case, a part of the zeolite-containing catalyst is taken out continuously or intermittently from the fluidized bed reactor and the coke adhered to the catalyst may be burned and removed using a gas containing oxygen. In so doing, the zeolite-containing catalyst is regenerated and the zeolite-containing catalyst after regeneration may be returned to the fluidized bed reactor. In general, the regeneration of the catalyst is carried out in air which is a gas containing oxygen or in an oxygen-containing gas atmosphere at 400 to 700° C.

The zeolite-containing catalyst of the present embodiment has a low void content and has good fluidity and high mechanical strength (attrition resistance). The production method, which is carried out by spray drying and calcining a specific raw material, is simple. Since the zeolite-containing catalyst of the present embodiment may be used for the production of propylene and has high mechanical strength, it is especially suitable as a catalyst for the fluidized bed reaction.

EXAMPLES

Hereinafter, the present invention will be described in detail by showing Examples, but the present invention is not limited to the following Examples.

[Measurement Methods of Various Physical Properties]

The measurement methods of various physical properties are as follows.

(1) Average Particle Diameter and Particle Size Distribution of Zeolite-Containing Catalyst The average particle diameter (cumulative particle diameter) and the particle size distribution of a zeolite-containing catalyst in a state after calcination were measured using a laser diffraction/scattering type particle size analyzer (manufactured by Microtrac Inc.; trade name, "MT3000") according to the attached catalog.

(2) Ratio of Void Area of Zeolite-Containing Catalyst

Firstly, the particles of the zeolite-containing catalyst after calcination are embedded with a polyester resin, followed by grinding to scrape away the cross-section of the catalyst particles. Subsequently, the cross-section of the catalyst particles which was scraped away was observed by an electron microscope (SEM; manufactured by Hitachi, Ltd.; trade name, "S-800") equipped with an image processing system (a high-definition image analysis filing system, manufactured by Asahi Chemical Industry Co., Ltd.; trade name, "IP-1000"). In this case, particles having a diameter in the range of ±10% of the average particle diameter were selected. For the selected particles, the cross-section area of one particle and the area of the void portion in the cross-section of the particle, which were observed by at a magnification of 800 to 2000 times, were measured by the image analysis device. Thereafter, the ratio of the area of the void portion to the cross-section area of the particles measured was calculated. Then, a series of operations were carried out for 100 particles and the arithmetic average (arithmetical mean) value was defined as the ratio of void area in the cross-section of particles.

In case of a slightly ellipsoidal particle and a particle having a distorted shape, the arithmetic average of the long diameter (the longest diameter among the diameters passing through the gravity center) and the short diameter (the shortest diameter among the diameters passing through the gravity center) was defined as a particle diameter. In addition, in case of the particle which has a shape in which a hole is ruptured and the cross-section is observed in a state (C-character shape) where a part of the circumference is cut, both ends of portions (opening portion) in which a part of the circumference is cut were connected with a straight line so as to occlude the opening portion, and the particle cross-section area and the area of the void portion were determined assuming that the straight line is a part of the outer circumference.

(3) Structure Type of Zeolite

The X-ray diffraction pattern of zeolite was measured using a powder X-ray diffraction apparatus (trade name, "RINT", manufactured by Rigaku Co., Ltd.) and the structure type was identified by referring to the well-known diffraction pattern of zeolite. The measurement conditions were set as follows: a Cu cathode, the tube voltage: 40 kv, the tube current: 30 mA, the scanning speed: 1 deg/min.

(4) Ratio $SiO_2/Al_2O_3$ (Molar Ratio) of Zeolite

A dissolution solution was prepared by completely dissolving zeolite in a sodium hydroxide solution. The amount of silicon and aluminum contained in the dissolution solution was measured by a conventional method using an ICP (inductive-coupled plasma) emission spectrometer (trade name "JY 138", manufactured by Rigaku Co., Ltd.), and from the results, the ratio of $SiO_2$ to $Al_2O_3$ (mole ratio) was derived. The measurement conditions were set as follows: the high frequency power: 1 kw, the plasma gas flow rate: 13 L/min, the sheath gas flow rate: 0.15 L/min, the nebulizer flow gas rate: 0.25 L/min, the silicone measurement wavelength: 251.60 nm, the aluminum measurement wavelength: 396.152 nm.

(5) Mechanical Strength of Particles of Zeolite-Containing Catalyst

The attrition loss, which is an indicator of mechanical strength of particles of a zeolite-containing catalyst, was measured using a jet fluidic apparatus. As the jet fluidic apparatus, there was used an apparatus, in which an orifice with three holes having a diameter of 0.4 mm was disposed at a gas introduction portion and which was equipped with a powder elevating portion having an inside diameter of 35 mm and a length of 700 mm, a powder separating portion having an inside diameter of 110 mm and a length of 600 mm and a fine powder collecting portion. Into the jet fluidic apparatus was charged 52.5 g of a zeolite-containing catalyst containing 2.5 g of moisture at room temperature, and then air containing moisture in an amount corresponding to the vapor pressure was circulated from a gas introduction portion at a rate of 5.8 NL/min, followed by measuring the mass of fine particles of the zeolite-containing catalyst, which were collected in a fine powder collecting portion for 0 to 5 hours and 5 to 20 hours after the start of measurement. And, the attrition loss was determined according to the following expression.

Attrition Resistance (% by mass)=$A/(B-C)\times100$

Here, in the above expression, A represents the mass (g) of the fine particles of the zeolite-containing catalyst collected for 5 to 20 hours after the start of measurement, C represents the mass (g) of the fine particles of the zeolite-containing catalyst collected for 0 to 5 hours after the start of measurement, and B represents the total mass (g) of the zeolite-containing catalyst used for the test.

(6) Fluidity of Zeolite-Containing Catalyst

The angle of repose, which is an indicator of the fluidity of the zeolite-containing catalyst, was measured using a cylinder rotating-type angle-of-repose measuring instrument (manufactured by Tsutsui Scientific Instruments Co., Ltd.). To a 500 cc glass sample container (cylindrical measurement bottle) was filled 250 cc of a zeolite-containing catalyst, and then the sample container was placed on the upper portion of a roller of the measuring instrument so that the side surface of the cylindrical measurement bottle is contacted with the roller and the central axis of the cylindrical measurement bottle is horizontal. Thereafter, while the roller portion was rotated around the central axis of the cylindrical measurement bottle at a rate of 2.4 rpm, the angle from the surface of a powder layer inside the cylindrical measurement bottle to the horizontal surface was measured.

(7) Sodium Content of Zeolite-Containing Catalyst

The content of sodium in a zeolite-containing catalyst after calcination and ion-exchange was measured as follows. Firstly, the catalyst was dissolved in royal water at 210° C. using a microwave (produced by Milestone Inc., Type: ETOS PLUS) and a small amount of residue was filtered. Thereafter, the sodium amount in the filtrate was measured by a conventional method using an ICP emission spectroscopy. From the result, the content of sodium in the zeolite-containing catalyst was derived. The measurement conditions was set as follows; the high frequency power: 1 kw, the plasma gas flow rate: 13 L/min, the sheath gas flow rate: 0.15 L/min: the nebulizer gas flow rate: 0.25 L/min, the sodium measurement wavelength: 589.592 nm.

(8) Calculation of Ethylene Conversion Rate and Propylene Yield

The ethylene conversion rate and the propylene yield were derived from the following expressions.

The Ethylene Conversion Rate=(The ethylene concentration in the feed flow at the reactor inlet−The ethylene concentration in the feed flow at the reactor outlet)/The ethylene concentration in the feed flow at the reactor inlet×100    (a)

The propylene Yield=The mass of propylene generated by the reaction/The mass of ethylene fed in the reactor×100    (b)

[Method for Obtaining Zeolite]

As for MFI-type ZSM-5 used in Examples 1, 5, 6 and 9 and Comparative Examples 1, 4 and 5, firstly, there were determined the amount of aluminum sulfate x-hydrate (produced by Wako Pure Chemical Industries, Ltd., special grade reagent) contained in A solution and the amount of water glass (trade name, "No. 3 Sodium Silicate"; produced by Fuji Kagaku Corp.; $SiO_2$: 29.0% by mass, $Na_2O$: 9.5% by mass, the balance: water) contained in B solution, so that the molar ratio $SiO_2/Al_2O_3$ of the zeolite is 280. Thereafter, A solution and B solution of that amount were mixed using a homogenizer at 5000 rpm for 30 minutes, followed by further hydrothermally synthesizing at 160° C. for three days (at a stirring rate of 600 rpm). Except for the above, zeolite was hydrothermally synthesized in the same manner as in Example 2 of Japanese Patent Publication No. 61-21985 (Japanese Patent Laid-Open No. 50-5335).

The resulting zeolite was sufficiently washed with water and dried at 120° C., followed by calcining under an air atmosphere in an electric furnace at 550° C. for 3 hours. Thereafter, in order to convert the cation type of the calcined zeolite into $NH_4^+$, the zeolite was ion exchanged using a 1 mol concentration of ammonium chloride aqueous solution at 25° C. for one hour, followed by further washing with water and drying at 120° C.

In addition, the ratio $SiO_2/Al_2O_3$ (molar ratio) of the MFI-type ZSM-5, which was measured by the above method, was 280, and the structure type was identified by the above method. The identification of the structure type was made by reference to the description in Japanese Patent Publication No. 46-10064 (the same shall apply hereinafter, unless otherwise specified).

As for MFI-type ZSM-5 used in Examples 2, 10, 11, 12, 13, 17, 23, 24 and 25 and Comparative Examples 2, 6, 7 and 9, firstly, zeolite was hydrothermally synthesized in the same manner as in Example 3 of Japanese Patent Publication No. 2-44771 (Japanese Patent Laid-Open No. 59-54620) except that a wet cake of the uniform compound D was prepared so that the molar ratio $SiO_2/Al_2O_3$ of the zeolite is 27.

The resulting zeolite was sufficiently washed with water and dried at 120° C. Thereafter, in order to convert the cation type of zeolite into $H^+$, the zeolite was ion-exchanged using a 1 mol concentration of nitric acid aqueous solution at 25° C. for one hour, followed by further washing with water and drying at 120° C.

In addition, the ratio $SiO_2/Al_2O_3$ (molar ratio) of the MFI-type ZSM-5, which was measured by the above method, was 27, and the structure type was identified by the above method.

The zeolite was subjected to pulverization treatment using a jet mill (manufactured by Nippon Pneumatic Mfg. Co., Ltd., Type: LJ) so that the average particle diameter is 3 μm because the primary particles are aggregated.

As for MFI-type ZSM-5 used in Examples 4 and 21, zeolite was hydrothermally synthesized in the same manner as in Example 3 of Japanese Patent Publication No. 2-44771 (Japanese Patent Laid-Open No. 59-54620) except that a wet cake of the uniform compound D was prepared so that the molar ratio $SiO_2/Al_2O_3$ of the zeolite is 42.

The resulting zeolite was sufficiently washed with water and dried at 120° C. Thereafter, in order to convert the cation type of zeolite into $H^+$, the zeolite was ion-exchanged using a 1 mol concentration of nitric acid aqueous solution at 25° C. for one hour, followed by further washing with water and drying at 120° C.

In addition, the ratio $SiO_2/Al_2O_3$ (molar ratio) of the MFI-type ZSM-5, which was measured by the above method, was 42, and the structure type was identified by the above method.

As for MFI-type ZSM-5 used in Examples 7, 8, 14, 15, 16, 18 and 19, firstly, there were determined the amount of aluminum sulfate x-hydrate (produced by Wako Pure Chemical Industries, Ltd., special grade reagent) contained in A solution and the amount of water glass (trade name, "No. 3 Sodium Silicate"; produced by Fuji Kagaku Corp.; $SiO_2$: 29.0% by mass, $Na_2O$: 9.5% by mass, the balance: water) contained in B solution, so that the molar ratio $SiO_2/Al_2O_3$ of the zeolite is 80. Thereafter, A solution and B solution of that amount were mixed using a homogenizer at 5000 rpm for 30 minutes, followed by further hydrothermally synthesizing at 160° C. for three days (at a stirring rate of 600 rpm). Except for the above, zeolite was hydrothermally synthesized in the same manner as in Example 2 of Japanese Patent Publication No. 61-21985 (Japanese Patent Laid-Open No. 50-5335.)

The resulting zeolite was sufficiently washed with water and dried at 120° C., followed by calcining under an air atmosphere in an electric furnace at 550° C. for 3 hours. Thereafter, in order to convert the cation type of the calcined zeolite into $NH_4^+$, the zeolite was ion exchanged using a 1 mol concentration of ammonium chloride aqueous solution at 25° C. for one hour, followed by further washing with water and drying at 120° C.

In addition, the ratio $SiO_2/Al_2O_3$ (molar ratio) of the MFI-type ZSM-5, which was measured by the above method, was 80, and the structure type was identified by the above method.

As for MFI-type ZSM-5 used in Example 3 and Comparative Example 3, "MFI-1000" (trade name) produced by Zeolyst International was used.

In addition, the ratio $SiO_2/Al_2O_3$ (molar ratio) of the MFI-type ZSM-5, which was measured by the above method, was 1000, and the structure type was identified by the above method.

As for BEA type Beta (β-type zeolite) used in Example 20, "BEA-25" (trade name) produced by PQ Corp. was used.

In addition, the ratio $SiO_2/Al_2O_3$ (molar ratio) of the β-type zeolite, which was measured by the above method, was 25, and the structure type was identified by the above method. The identification of the structure type was made by reference to the description in the specification of U.S. Pat. No. 3,308,069.

As for MFI-type ZSM-5 used in Example 22, zeolite was hydrothermally synthesized according to Example 4 of JP Patent No. 3905948. The ratio $SiO_2/Al_2O_3$ (molar ratio) of the MFI-type ZSM-5, which was measured by the above method, was 39, and the structure type was identified by the above method.

As for an ultrastable Y-type (USY) zeolite used in Comparative Example 8, zeolite produced by Tosoh Corporation was used.

Example 1

To 2000 g of a colloidal silica (produced by Nalco Company, the silica average particle diameter: 5 nm, the silica content rate: 15% by mass, the sodium content: 185 ppm) was added 40 g of nitric acid (Wako Pure Chemical Industries, Ltd., a reagent containing 60% by mass of nitric acid, the same shall apply hereinafter) to adjust the pH to 1.1. Thereafter, to the mixture was added 100 g of ammonium nitrate (Wako Pure Chemical Industries, Ltd., special grade reagent, the solubility in water at 0° C.: 118 g/100 g of water, the same shall apply hereinafter), which is a water-soluble compound. Subsequently, to the resulting mixture was added 300 g of MFI-type ZSM-5, in which the molar ratio $SiO_2/Al_2O_3$ of the zeolite is 280, to prepare a raw material slurry (a preparation step of a raw material mixture). The resulting raw material slurry was stirred at 25° C. for 3 hours. The raw material slurry exhibited a sol state and had a viscosity of 5 cP (measured by a B-type viscometer, manufactured by Tokyo Keiki Inc.) The raw material slurry was spray-dried with a spray dryer to obtain a dried powder (a drying step). The raw material slurry was spray dried using a rotating disk method by setting the fluid temperature at the spray dryer inlet at 220° C. and the fluid temperature at the spray dryer outlet at 130° C. The resulting dried powders were calcined using an electric furnace under an air atmosphere at 700° C. for 5 hours (a calcination step).

The resulting calcined powders were mixed with a 0.1 mol concentration of nitric acid aqueous solution to adjust the solid content concentration to 10% by mass, followed by subjecting to ion-exchange treatment at 25° C. for one hour (an ion-exchange step). Thereafter, the ion-exchanged powders through the ion-exchange step were sufficiently washed with water and dried at 120° C.

Figure 2:
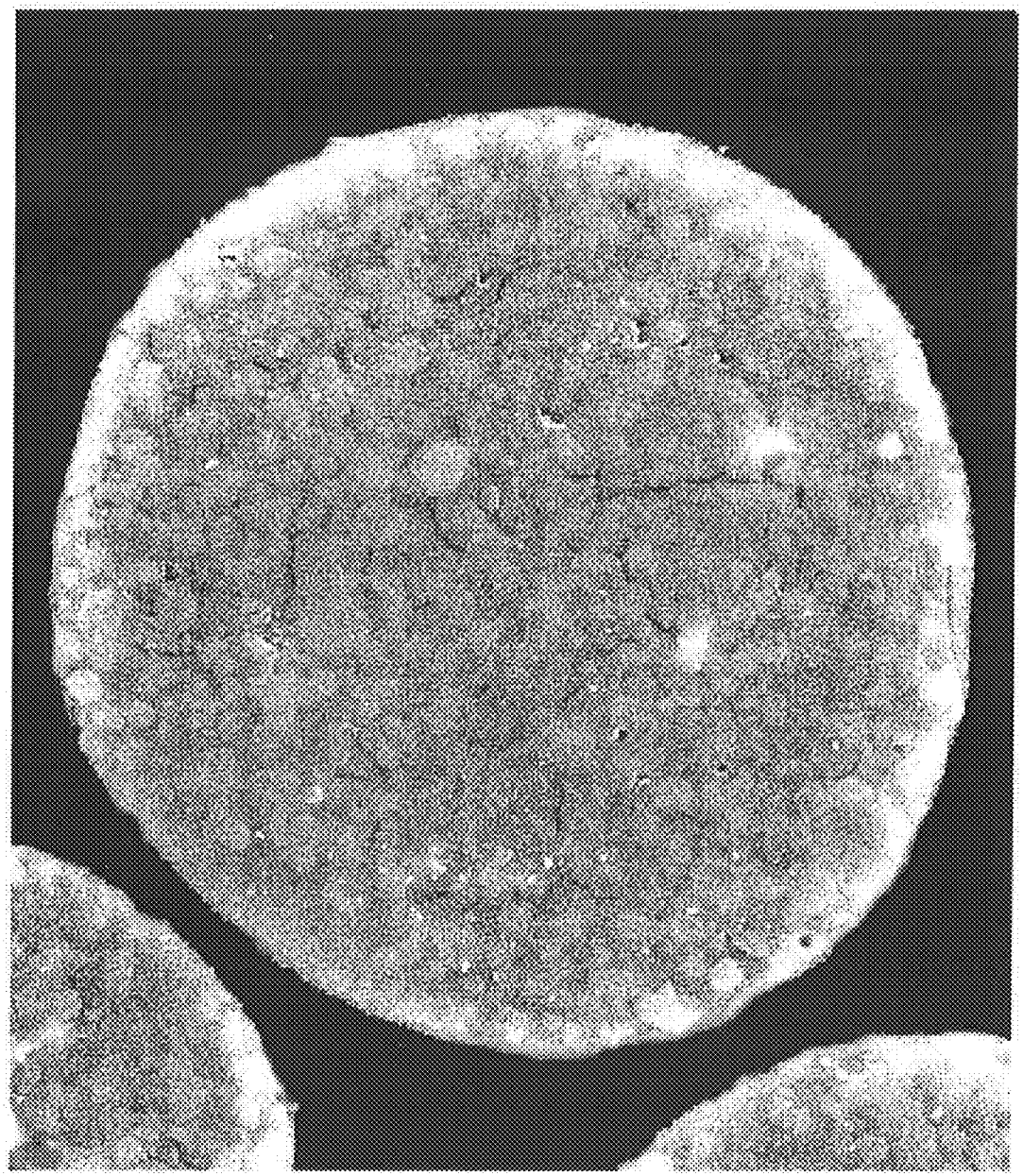
FIG. 2 is an electron microscope photograph (at a magnification of 1500 times) showing a particle cross-section of the zeolite-containing catalyst of Example 1.

On the zeolite-containing catalyst thus obtained, measurements were made, which included the average particle diameter, angle of repose, mechanical strength (attrition loss) and ratio of void area in the catalyst particle cross-section in the shape after the calcination (calcined product) as well as the sodium content in the shape after the calcination and after the ion-exchange (ion-exchanged powders), according to the above-described methods. In addition, the content rate of zeolite, silica and other components was calculated from the feed ratio (the same shall apply hereinafter). The measurements values are shown in Table 1. Further, the electron microscope photograph of the catalyst particles is shown in FIG. 1, and the electron microscope photograph of the catalyst particle cross-section is shown in FIG. 2. The calcined particles had a particle size distribution in which 95% particles in the whole particles on a volume basis are in the particle diameter range of 2 to 0.2 times the average particle diameter.

Example 2

A zeolite-containing catalyst was prepared in the same manner as in Example 1 except for replacing the zeolite with MFI-type ZSM-5 in which the molar ratio $SiO_2/Al_2O_3$ is 27.

Figure 3:
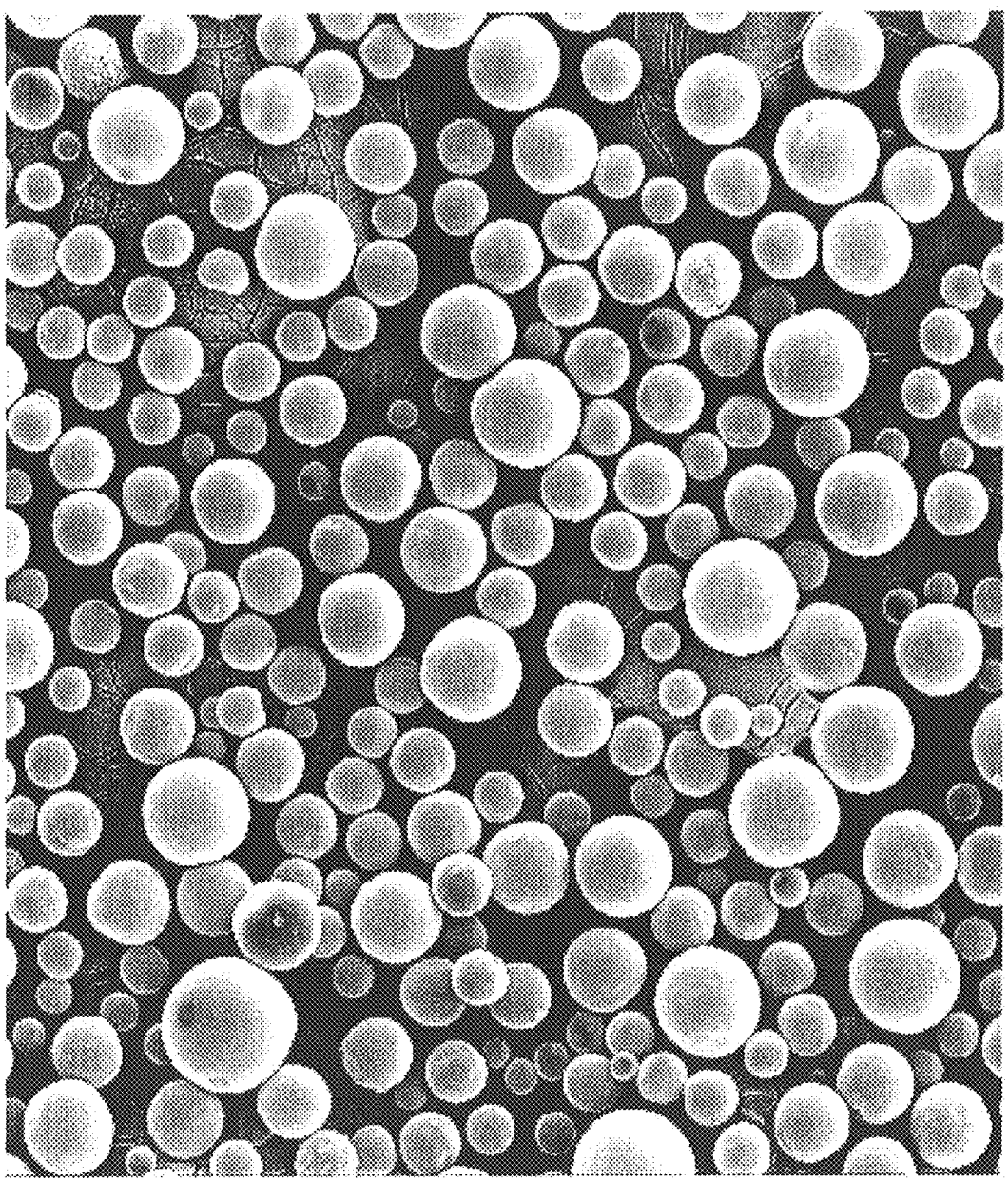
FIG. 3 is an electron microscope photograph (at a magnification of 150 times) showing a zeolite-containing catalyst of Example 2.
Figure 4:
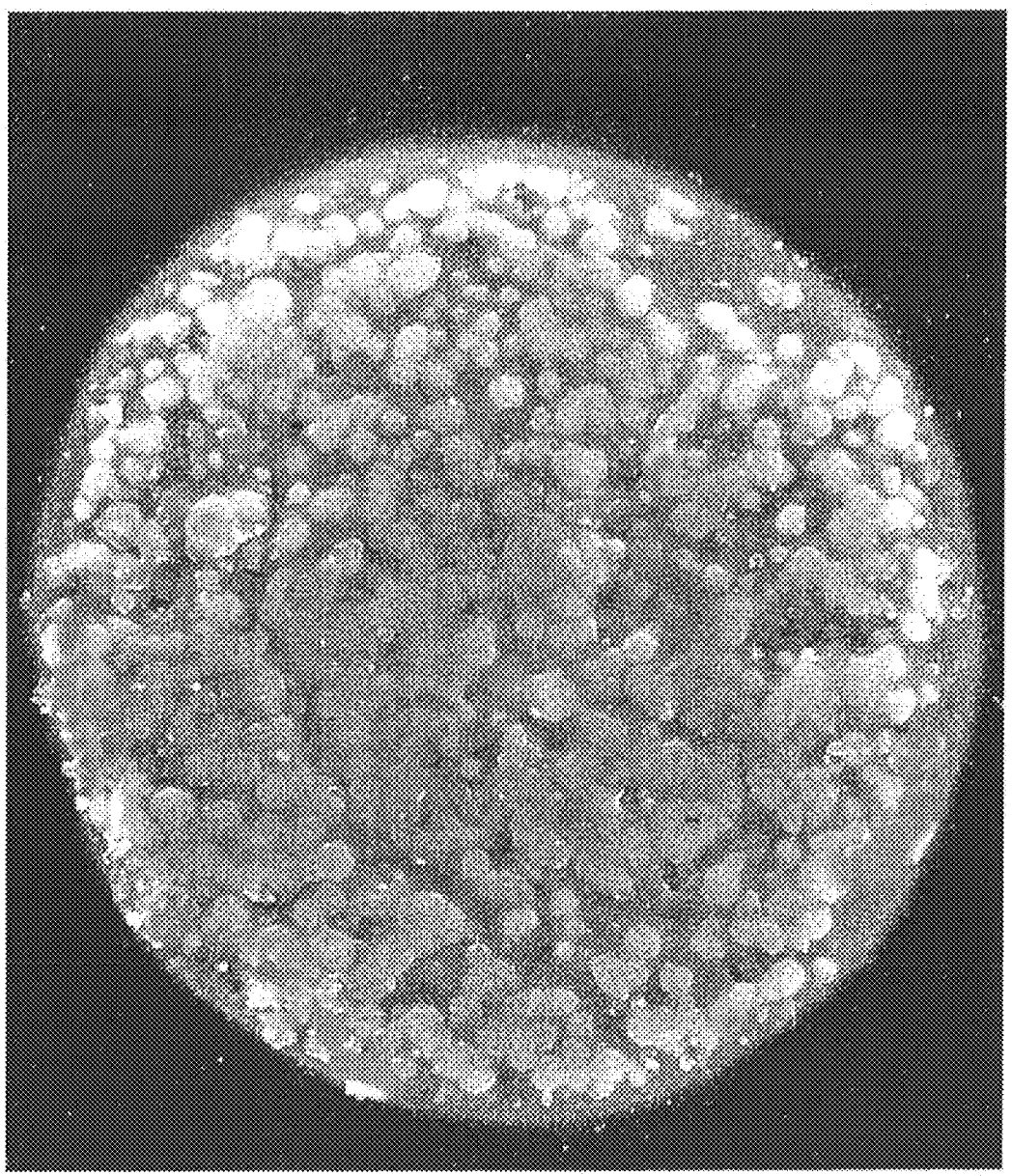
FIG. 4 is an electron microscope photograph (at a magnification of 1700 times) showing a particle cross-section of the zeolite-containing catalyst of Example 2.
Figure 7:
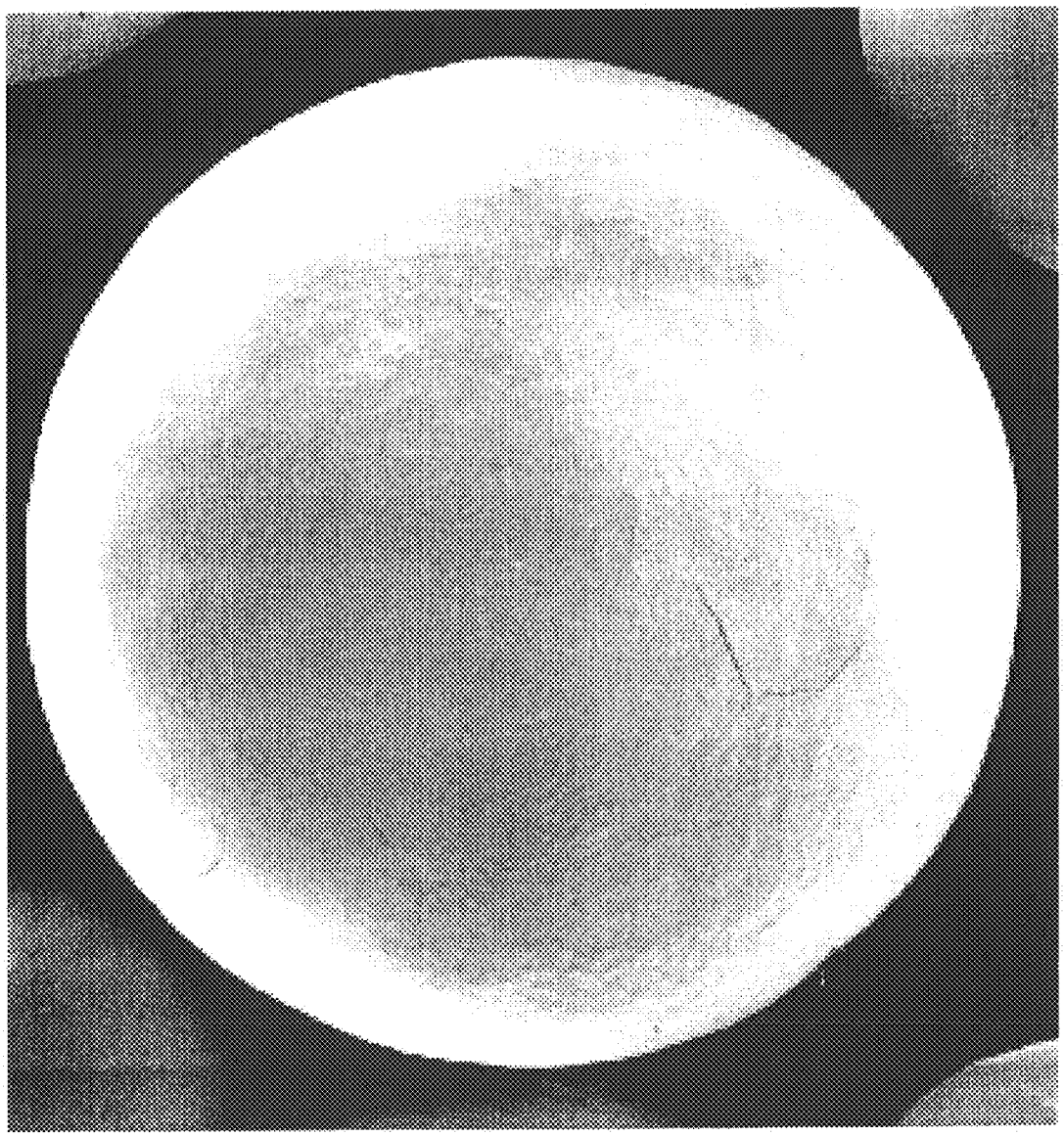
FIG. 7 is an electron microscope photograph (at a magnification of 1700 times) showing a particle surface of the zeolite-containing catalyst of Example 2.

On the zeolite-containing catalyst thus obtained, the above various physical properties in the shape after the calcination and ion-exchange were measured. The measurement values are shown in Table 1. In addition, the electron microscope photograph of the catalyst particles is shown in FIG. 3, and the electron microscope photograph of the catalyst particle cross-section is shown in FIG. 4. Further, the electron microscope photograph of the catalyst particle surface is shown in FIG. 7. A thin crack was observed on the particle surface but the surface had no unevenness.

Example 3

A zeolite-containing catalyst was prepared in the same manner as in Example 1 except for replacing the zeolite with MFI-type ZSM-5 in which the molar ratio $SiO_2/Al_2O_3$ is 1000.

Figure 5:
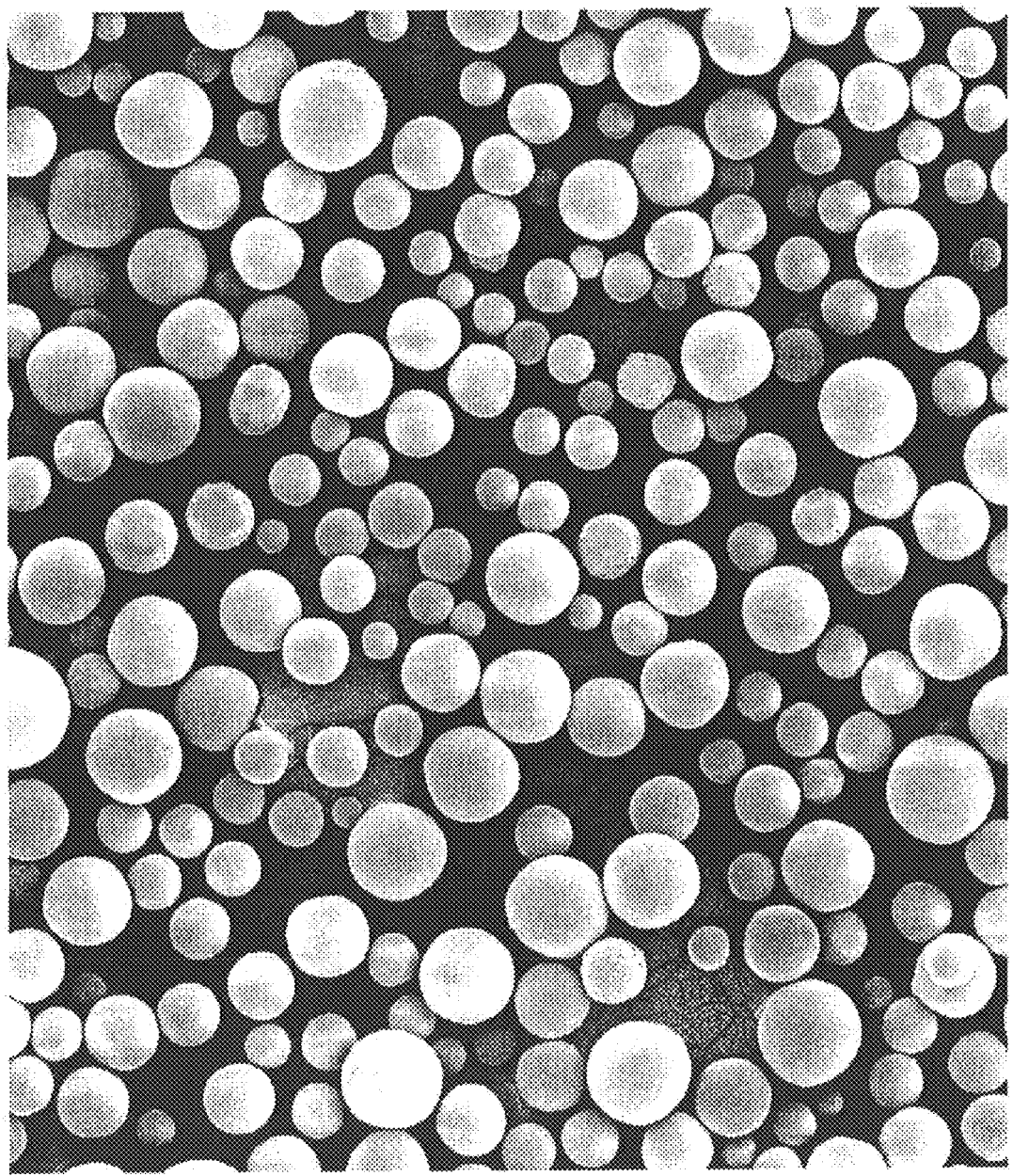
FIG. 5 is an electron microscope photograph (at a magnification of 150 times) showing a zeolite-containing catalyst of Example 3.
Figure 6:
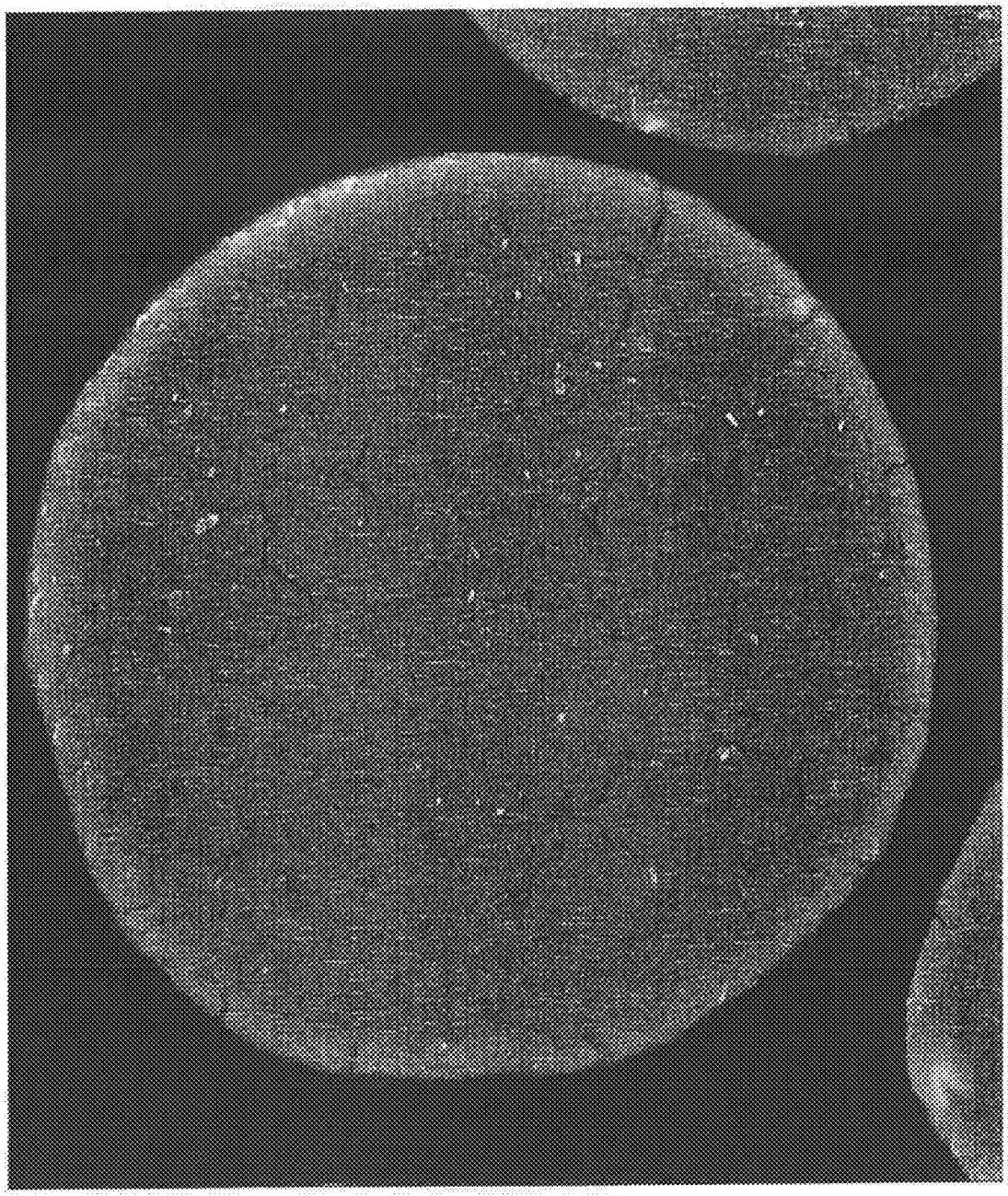
FIG. 6 is an electron microscope photograph (at a magnification of 1600 times) showing a particle cross-section of the zeolite-containing catalyst of Example 3.

On the zeolite-containing catalyst thus obtained, the above various physical properties in the shape after the calcination and ion-exchange were measured. The measurement values are shown in Table 1. In addition, the electron microscope photograph of the catalyst particles is shown in FIG. 5, and the electron microscope photograph of the catalyst particle cross-section is shown in FIG. 6.

Example 4

A zeolite-containing catalyst was prepared in the same manner as in Example 1 except for replacing the zeolite with MFI-type ZSM-5 in which the molar ratio $SiO_2/Al_2O_3$ is 42.

On the zeolite-containing catalyst thus obtained, the above various physical properties in the shape after the calcination and ion-exchange were measured. The measurement values are shown in Table 1.

Example 5

A zeolite-containing catalyst was prepared in the same manner as in Example 1 except for replacing the water-soluble compound with ammonium acetate (produced by Wako Pure Chemical Industries, Ltd., special grade reagent, the solubility in water at 4° C.: 148 g/100 g of water).

On the zeolite-containing catalyst thus obtained, the above various physical properties in the shape after the calcination and ion-exchange were measured. The measurement values are shown in Table 1.

Example 6

A zeolite-containing catalyst was prepared in the same manner as in Example 1 except for replacing the colloidal silica with 795 g of a colloidal silica (produced by Nalco Company, a wide range particle distribution type, the silica average particle diameter: 15 nm, the silica content rate: 38% by mass, the sodium content: 300 ppm) and replacing the water-soluble compound with ammonium sulfate (produced by Wako Pure Chemical Industries, Ltd., special grade reagent, the solubility in water at 0° C.: 71 g/100 g of water). In addition, purified water was arbitrarily added to the raw material slurry so that the solid content concentration of the raw material slurry immediately before spray drying is 30% by mass.

On the zeolite-containing catalyst thus obtained, the above various physical properties in the shape after the calcination and ion-exchange were measured. The measurement values are shown in Table 1.

Example 7

A zeolite-containing catalyst was prepared in the same manner as in Example 1 except for replacing the zeolite with MFI-type ZSM-5 in which the molar ratio $SiO_2/Al_2O_3$ is 80 and replacing the water-soluble compound with 72 g of ammonium chloride (produced by Wako Pure Chemical Industries, Ltd., special grade reagent, the solubility in water at 0° C.: 29 g/100 g of water).

On the zeolite-containing catalyst thus obtained, the above various physical properties in the shape after the calcination and ion-exchange were measured. The measurement values are shown in Table 1.

Example 8

A zeolite-containing catalyst was prepared in the same manner as in Example 7 except for replacing the water-soluble compound with 60 g of ammonium carbonate (produced by Wako Pure Chemical Industries, Ltd., special grade reagent, the solubility in water at 15° C.: 25 g/100 g of water).

On the zeolite-containing catalyst thus obtained, the above various physical properties in the shape after the calcination and ion-exchange were measured. The measurement values are shown in Table 1.

Example 9

A zeolite-containing catalyst was prepared in the same manner as in Example 1 except for replacing the colloidal silica with 1800 g of a colloidal silica (produced by Nalco Company, the silica average particle diameter: 5 nm, the silica content rate: 15% by mass, the sodium content: 185 ppm) and replacing the water-soluble compound with 221 g of aluminum nitrate 9-hydrate (produced by Wako Pure Chemical Industries, Ltd., special grade reagent, the solubility in water at 25° C.: 77.5 g/100 g of water).

On the zeolite-containing catalyst thus obtained, the above various physical properties in the shape after the calcination and ion-exchange were measured. The measurement values are shown in Table 2.

Example 10

A zeolite-containing catalyst was prepared in the same manner as in Example 2 except for replacing the water-soluble compound with 106 g of sodium nitrate (produced by Wako Pure Chemical Industries, Ltd., special grade reagent, the solubility in water at 0° C.: 73 g/100 g of water).

On the zeolite-containing catalyst thus obtained, the above various physical properties in the shape after the calcination and ion-exchange were measured. The measurement values are shown in Table 2.

Example 11

A zeolite-containing catalyst was prepared in the same manner as in Example 2 except that, in order to reduce the average particle diameter of the zeolite-containing catalyst, the rotation number of the rotating disk in spray drying the raw material slurry in the drying step was increased.

On the zeolite-containing catalyst thus obtained, the above various physical properties in the shape after the calcination and ion-exchange were measured. The measurement values are shown in Table 2. The zeolite-containing catalyst had an average particle diameter of 21 μm.

Example 12

A zeolite-containing catalyst was prepared in the same manner as in Example 2 except that, in order to increase the average particle diameter of the zeolite-containing catalyst, the rotation number of the rotating disk in spray drying the raw material slurry in the drying step was decreased.

On the zeolite-containing catalyst thus obtained, the above various physical properties in the shape after the calcination and ion-exchange were measured. The measurement values are shown in Table 2. The zeolite-containing catalyst had an average particle diameter of 87 μm.

Example 13

A zeolite-containing catalyst was prepared in the same manner as in Example 2 except that, in order to increase the average particle diameter of the zeolite-containing catalyst, the rotation number of the rotating disk in spray drying the raw material slurry and the feed amount of the raw material slurry in the drying step were decreased.

On the zeolite-containing catalyst thus obtained, the above various physical properties in the shape after the calcination and ion-exchange were measured. The measurement values are shown in Table 2. The zeolite-containing catalyst had an average particle diameter of 293 μm.

Example 14

A zeolite-containing catalyst was prepared in the same manner as in Example 1 except for replacing the zeolite with MFI-type ZSM-5 in which the molar ratio $SiO_2/Al_2O_3$ is 80 and changing the amount of water-soluble compound to 10 g of ammonium nitrate.

On the zeolite-containing catalyst thus obtained, the above various physical properties in the shape after the calcination and ion-exchange were measured. The measurement values are shown in Table 2.

Example 15

A zeolite-containing catalyst was prepared in the same manner as in Example 14 except for changing the amount of the water-soluble compound to 30 g of ammonium nitrate.

On the zeolite-containing catalyst thus obtained, the above various physical properties in the shape after the calcination and ion-exchange were measured. The measurement values are shown in Table 2.

Example 16

A zeolite-containing catalyst was prepared in the same manner as in Example 14 except for changing the amount of the water-soluble compound to 1440 g of ammonium nitrate.

On the zeolite-containing catalyst thus obtained, the above various physical properties in the shape after the calcination and ion-exchange were measured. The measurement values are shown in Table 2.

Example 17

A zeolite-containing catalyst was prepared in the same manner as in Example 2 except for replacing the colloidal silica with 1235 g of a colloidal silica (produced by Nalco Company, the silica average particle diameter: 12 nm, the silica content rate: 34% by mass, the sodium content: 12 ppm), changing the amount of the water-soluble compound to 140 g of ammonium nitrate and changing the amount of MFI-type ZSM-5, in which the molar ratio $SiO_2/Al_2O_3$ of the zeolite is 27, to 180 g.

On the zeolite-containing catalyst thus obtained, the above various physical properties in the shape after the calcination and ion-exchange were measured. The measurement values are shown in Table 3.

Example 18

To 3800 g of a colloidal silica (produced by Nalco Company, the silica average particle diameter: 5 nm, the silica content rate: 15% by mass, the sodium content: 185 ppm) was added 60 g of nitric acid to adjust the pH to 1.5. Thereafter, to the mixture was added 188 g of ammonium nitrate, which is a water-soluble compound. Subsequently, to the resulting mixture was added 30 g of MFI-type ZSM-5, in which the molar ratio $SiO_2/Al_2O_3$ of the zeolite is 80, to prepare a raw material slurry. Except for the above, a zeolite-containing catalyst was prepared in the same manner as in Example 1.

On the zeolite-containing catalyst thus obtained, the above various physical properties in the shape after the calcination and ion-exchange were measured. The measurement values are shown in Table 3.

Example 19

A zeolite-containing catalyst was prepared in the same manner as in Example 18 except for replacing the colloidal silica with 1200 g of a colloidal silica (produced by Nalco Company, the silica average particle diameter: 5 nm, the silica content rate: 15% by mass, the sodium content: 185 ppm), changing the addition amount of nitric acid to 24 g, changing the amount of the water-soluble compound to 60 g of ammonium nitrate and changing the amount of MFI-type ZSM-5, in which the molar ratio $SiO_2/Al_2O_3$ is 80, to 420 g.

On the zeolite-containing catalyst thus obtained, the above various physical properties in the shape after the calcination and ion-exchange were measured. The measurement values are shown in Table 3.

Example 20

In the preparation step of the raw material mixture, to a 2800 g of a colloidal silica (produced by Nalco Company, the silica average particle diameter: 5 nm, the silica content rate: 15% by mass, the sodium content: 185 ppm) was added 56 g of nitric acid to adjust the pH to 0.9. To the mixture was added 140 g of ammonium nitrate as a water-soluble compound. Thereafter, to the resulting mixture was added 180 g of a β-type zeolite, in which the molar ratio $SiO_2/Al_2O_3$ of the zeolite is 25, to prepare a raw material slurry. Except for the above, a zeolite-containing catalyst was prepared in the same manner as in Example 1.

On the zeolite-containing catalyst thus obtained, the above various physical properties in the shape after the calcination and ion-exchange were measured. The measurement values are shown in Table 3.

Example 21

A mixture was prepared by adding 300 g of MFI-type ZSM-5, in which the molar ratio $SiO_2/Al_2O_3$ of the zeolite is 42, to 2000 g of a colloidal silica (produced by Nalco Company, the silica average particle diameter: 5 nm, the silica content rate: 15% by mass, the sodium content: 185 ppm). To the mixture was added 40 g of nitric acid to adjust the pH to 1.2. Thereafter, to the resulting mixture was added 100 g of ammonium nitrate, which is a water-soluble compound, to obtain a raw material slurry (a preparation step of a raw material mixture). A zeolite-containing catalyst was prepared in the same way as in Example 1 in the steps that followed.

On the zeolite-containing catalyst thus obtained, the above various physical properties in the shape after the calcination and ion-exchange were measured. The measurement values are shown in Table 3.

Example 22

According to Example 4 of JP Patent No. 3905948, an MFI-type ZSM-5 zeolite (the molar ratio $SiO_2/Al_2O_3$ is 39) was hydrothermally synthesized. This zeolite slurry as in a slurry state was washed with water using a rotary filter until the pH becomes 9. Further, the slurry was ion-exchanged with a 1 mol concentration of sulfuric acid aqueous solution at 25° C. for one hour and then washed with water until the pH becomes 4 to obtain 29% by mass of an $H^+$ type MFI-type ZSM-5 zeolite-containing slurry. A zeolite-containing catalyst was prepared in the same manner as in Example 1 except for using 1034 g of this slurry (containing 300 g of zeolite) as a raw material zeolite and changing the amount of ammonium nitrate which is a water-soluble compound to 60 g.

On the zeolite-containing catalyst thus obtained, the above various physical properties in the shape after the calcination and ion-exchange were measured. The measurement values are shown in Table 3.

Example 23

To a 1500 g of a colloidal silica (produced by Nalco Company, the silica average particle diameter: 5 nm, the silica content rate: 15% by mass, the sodium content: 185 ppm) was added 98 g of nitric acid to adjust the pH to 0.3. To the mixture was added 75 g of ammonium nitrate, which is a water-soluble compound. Thereafter, to the resulting mixture was added an aqueous solution obtained by diluting 300 g of water glass (trade name, "Special No. 3 Sodium Silicate"; produced by Fuji Kagaku Corp.; $SiO_2$: 25.0% by mass, $Na_2O$: 9.0% by mass, the balance: water, the same shall apply hereinafter) with 200 g of purified water. In addition, in this silica sol, 75% by mass of the silica component is made from the colloidal silica and 25% by mass of the silica component is made from water glass. To the mixture was added 300 g of MFI-type ZSM-5, in which the molar ratio $SiO_2/Al_2O_3$ of the zeolite is 27, to prepare raw material slurry. The raw material slurry had a pH of 1.1.

The raw material slurry was spray dried in the same manner as in Example 1. The resulting dried powders were washed with water at 60 to 85° C. for one hour while stirring with 10 L of purified water. This operation was repeated two times. Subsequently, the solid content concentration was adjusted to 10% by mass with a 1 mol concentration of nitric acid aqueous solution, followed by ion-exchanging at 60 to 85° C. for one hour. This operation was repeated two times. Thereafter, the resulting slurry was sufficiently washed with water and dried at 120° C.

The resulting dried powders were calcined using an electric furnace under an air atmosphere at 700° C. for one hour.

On the zeolite-containing catalyst thus obtained, the above various physical properties in the shape after the ion-exchange and calcination were measured. The measurement values are shown in Table 3.

In addition, for reference, a part of the dried powders was collected and the sodium content before ion-exchange was measured to be 3.27% by mass.

Example 24

There was prepared MFI-type ZSM-5 in which ammonium phosphate was supported on MFI-type ZSM-5 (the molar ratio $SiO_2/Al_2O_3$ is 27) used in Example 2 in the following manner. Firstly, a solution was prepared by dissolving 72.2 g of ammonium phosphate (produced by Wako Pure Chemical Industries, Ltd., special grade reagent) in 1 L of purified water. To the solution was added 500 g of the zeolite. Water was distilled off from the resulting slurry by an evaporator under reduced pressure at 60° C. over approximately one hour, and the remaining solid content was collected and dried, followed by calcining at 500° C. for one hour. A zeolite-containing catalyst was prepared in the same manner as in Example 2 except for replacing the zeolite with 300 g of MFI-type ZSM-5 on which the phosphorous component was supported and changing the amount of ammonium nitrate which is a water-soluble compound to 150 g.

On the zeolite-containing catalyst thus obtained, the above various physical properties in the shape after the calcination and ion-exchange were measured. The measurement values are shown in Table 3.

Example 25

To a 1200 g of a colloidal silica (produced by Nalco Company, the silica average particle diameter: 5 nm, the silica content rate: 15% by mass, the sodium content: 185 ppm) was added 160 g of nitric acid to adjust the pH to 0.1. To the mixture was added 59 g of ammonium nitrate, which is a water-soluble compound. Thereafter, to the resulting mixture was added an aqueous solution obtained by diluting 480 g of water glass (trade name "Special No. 3 Sodium Silicate", produced by Fuji Kagaku Corp.) with 400 g of purified water. In addition, in this silica sol, 60% by mass of the silica component is made from the colloidal silica and 40% by mass of the silica component is made from water glass. To the mixture was added 300 g of MFI-type ZSM-5, in which the molar ratio SiO$_2$/Al$_2$O$_3$ of the zeolite is 27, to prepare a raw material slurry. The raw material slurry had a pH of 0.5.

A zeolite-containing catalyst was prepared in the same manner as in Example 23 after the step of spray drying the raw material slurry.

On the zeolite-containing catalyst thus obtained, the above various physical properties in the shape after the calcination and ion-exchange were measured. The measurement values are shown in Table 3.

In addition, for reference, a part of the dried powders was collected and the sodium content before ion-exchange was measured to be 5.11% by mass.

Figure 8:
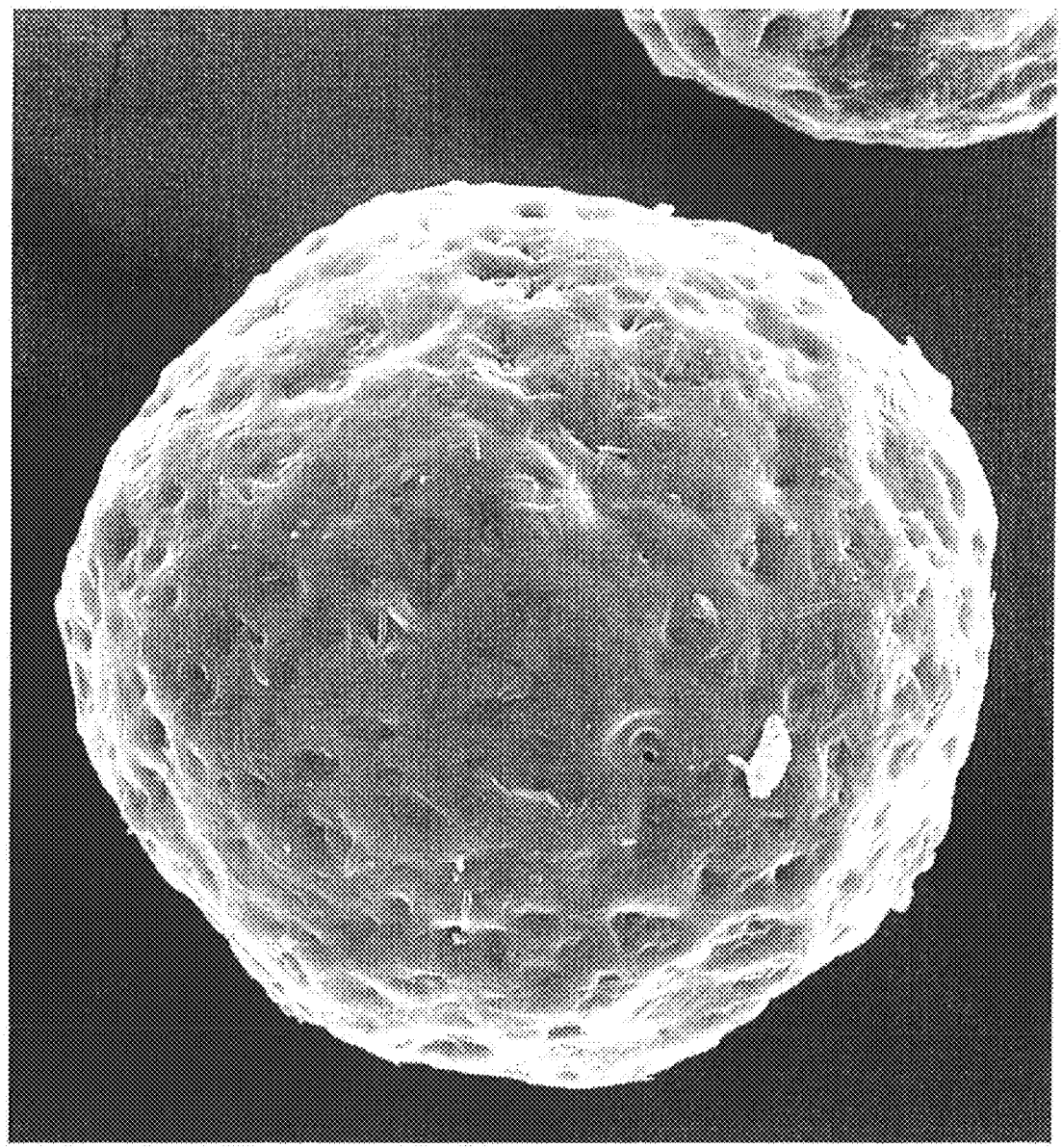
FIG. 8 is an electron microscope photograph (at a magnification of 1600 times) showing a particle surface of the zeolite-containing catalyst of Example 25.

Further, the electron microscope photograph of the catalyst particle surface is shown in FIG. 8.

Example 26

Figure 9:
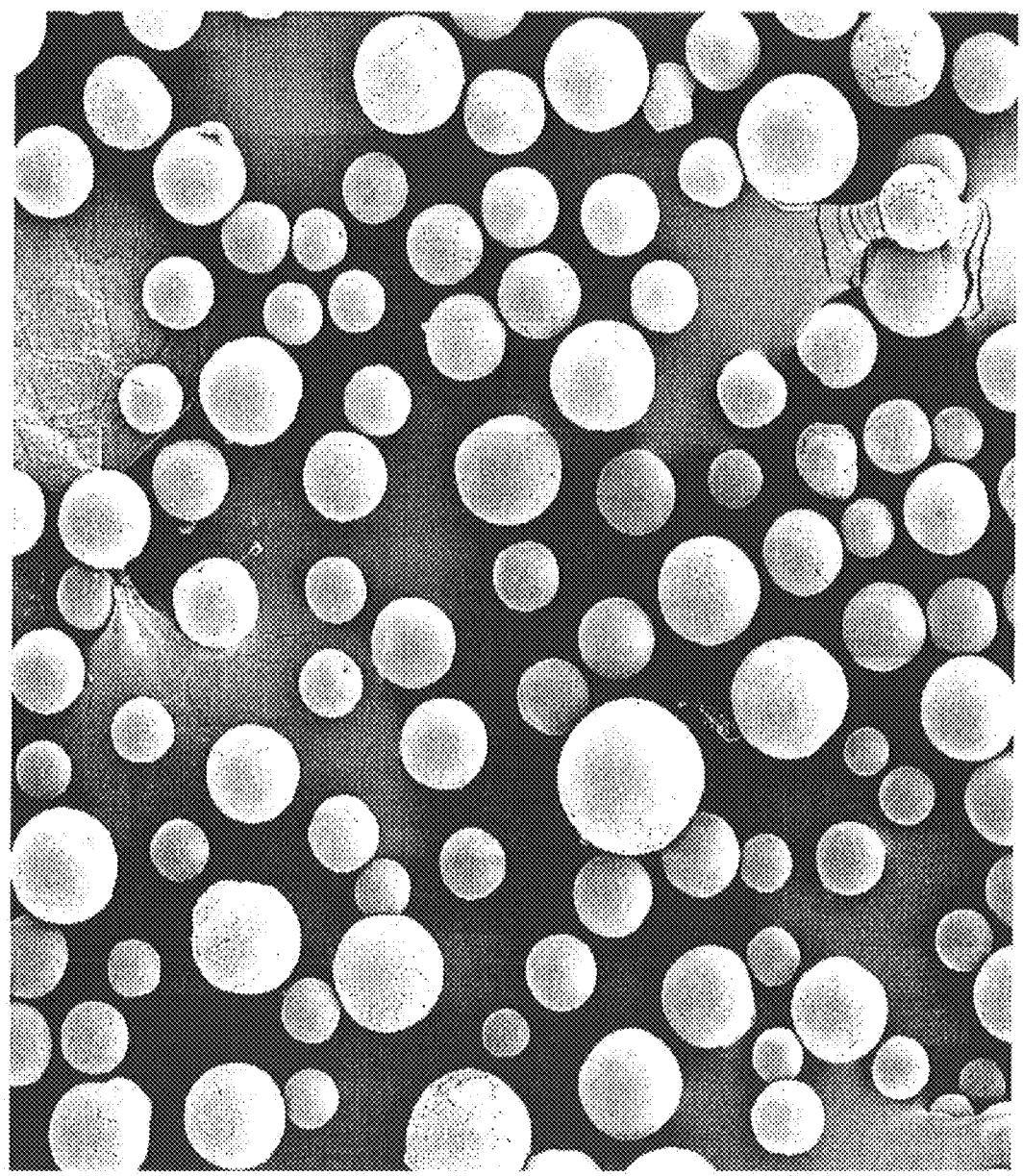
FIG. 9 is an electron microscope photograph (at a magnification of 150 times) showing a zeolite-containing catalyst of Example 26 after operation for 1000 hours.

There was produced 500 kg of a zeolite-containing catalyst in the same manner as in Example 2. The catalyst was filled in a fluidized bed reactor cold model apparatus made of transparent vinyl chloride (the inside diameter: 60 cm, the height: 5 m) which is equipped with a cyclone portion. Thereafter, air was fed by a blower from the lower portion of the equipment at a rate of 700 m$^3$/hr, and the equipment was continuously operated for 1000 hours while fluidizing the catalyst at a gas linear velocity of 70 cm/sec (on an empty tower basis), which is on a par with an industrial operational condition of a fluidized bed reaction. The catalyst had an attrition loss of 0.20% by mass and an average particle diameter of 58 μm after the operation for 1000 hours, and powderization, cracking or chipping of the catalyst was not almost observed, thereby enabling to continue the operation stably under the industrial operational condition of the fluidized bed reaction. The electron microscope photograph of the catalyst after the operation for 1000 hours is shown in FIG. 9.

Production of Propylene

Example 27

Figure 18:
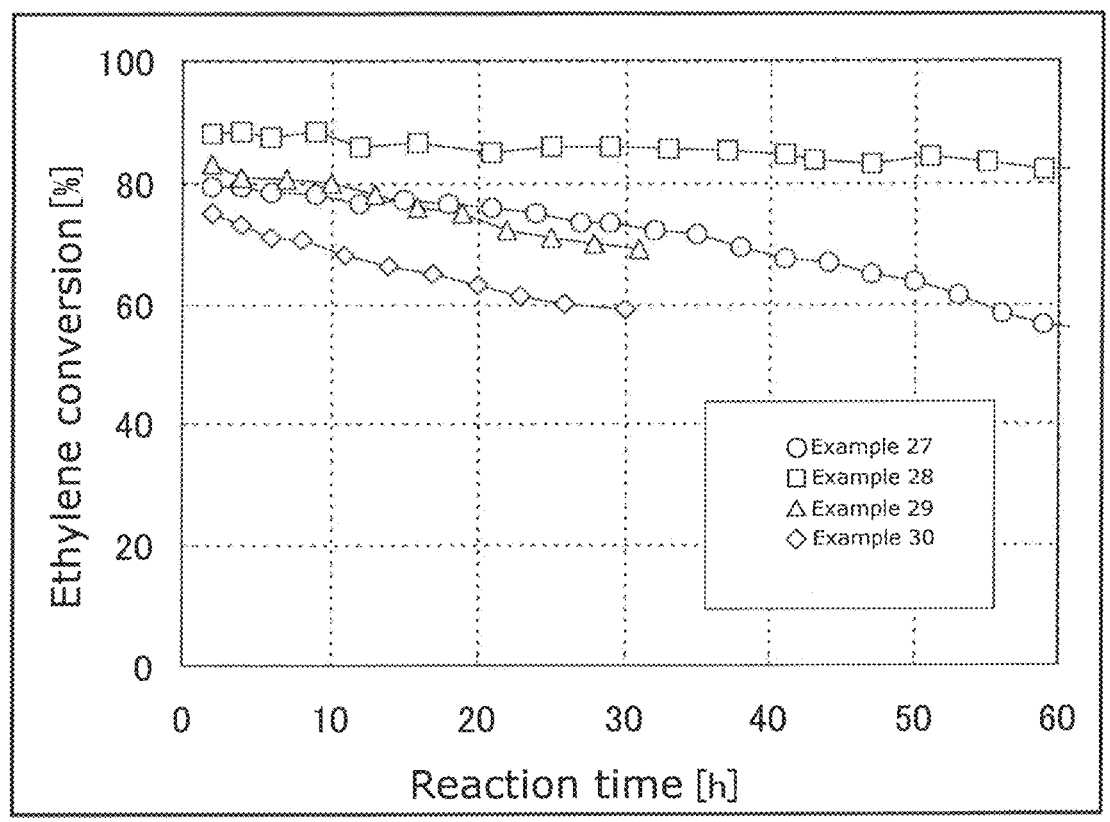
FIG. 18 shows the change over time of the ethylene conversion rate when performing a reaction for producing propylene from a raw material containing ethylene in Examples 27 to 30.

The zeolite-containing catalyst obtained in Example 2 was subjected to steaming treatment under the conditions of 650° C., 24 hours, a vapor partial pressure of 0.8 atm and a nitrogen gas partial pressure of 0.2 atm. To a stainless steel fluidized bed reactor having an inside diameter of 1 inch was filled 22.9 g of the catalyst. Thereafter, the fluidized bed reaction was carried out for 100 hours by feeding ethylene, hydrogen, water and nitrogen at a flow rate of 9.9 g/hr, 0.7 g/hr, 4.9 g/hr and 5.3 g/hr, respectively, under the conditions of a reaction temperature of 550° C., a reaction pressure of 0.14 MPa, a WHSV of 0.43 hr$^{-1}$ (on a zeolite-containing catalyst basis). During the reaction, powderization of the catalyst was not at all observed. The analysis of the reaction product was carried out by a gas chromatography (GC-17A, TCD-FID series connection type, manufactured by Shimadzu Corporation) directly connected to the reactor. The process of the ethylene conversion rate at each reaction time is shown in FIG. 18. The propylene yield in the ethylene conversion rate of 70% was 24.5% by mass.

Example 28

In order to remove the excessive phosphorous component from the zeolite-containing catalyst obtained in Example 24, the catalyst was washed with water at 25° C. for one hour. The zeolite-containing catalyst after water washing was subjected to steaming treatment under the same conditions as in Example 27. The fluidized bed reaction was carried out using 22.9 g of the catalyst in the same manner as in Example 27. The process of the ethylene conversion rate at each reaction time is shown in FIG. 18. The propylene yield in the ethylene conversion rate of 70% was 25.5% by mass.

Example 29

The zeolite-containing catalyst after calcination, which was obtained in the same manner as in Example 17 except that the ion-exchange was not carried out, was subjected to steaming treatment under the conditions of 560° C., 12 hours, a vapor partial pressure of 0.8 atm and a nitrogen gas partial pressure of 0.2 atm. The fluidized bed reaction was carried out using 22.9 g of the catalyst in the same manner as in Example 17. The process of the ethylene conversion rate at each reaction time is shown in FIG. 18. The propylene yield in the ethylene conversion rate of 70% was 23.0% by mass.

Example 30

The zeolite-containing catalyst obtained in Example 25 was subjected to steaming treatment under the same conditions as in Example 27. The fluidized bed reaction was carried out using 22.9 g of the catalyst in the same manner as in Example 27. The process of the ethylene conversion rate at each reaction time is shown in FIG. 18. The propylene yield in the ethylene conversion rate of 70% was 24.0% by mass.

Example 31

Figure 19:
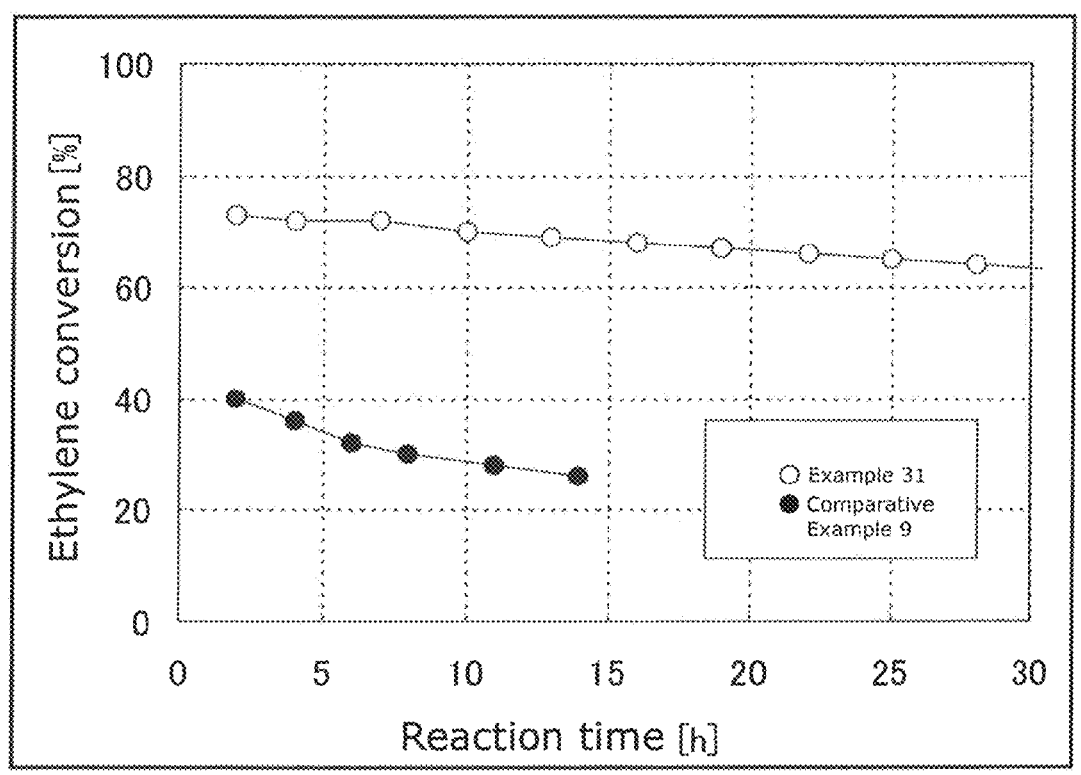
FIG. 19 shows the change over time of the ethylene conversion rate when performing a reaction for producing propylene from a raw material containing ethylene in Example 31 and Comparative Example 9.

The zeolite-containing catalyst obtained in Example 17 was subjected to steaming treatment under the same conditions as in Example 27. The fluidized bed reaction was carried out using 22.9 g of the catalyst in the same manner as in Example 27. The process of the ethylene conversion rate at each reaction time is shown in FIG. 19. The propylene yield in the ethylene conversion rate of 70% was 24.2% by mass.

Comparative Example 1

A zeolite-containing catalyst was prepared in the same manner as in Example 1 except that ammonium nitrate was not added to the raw material slurry.

Figure 10:
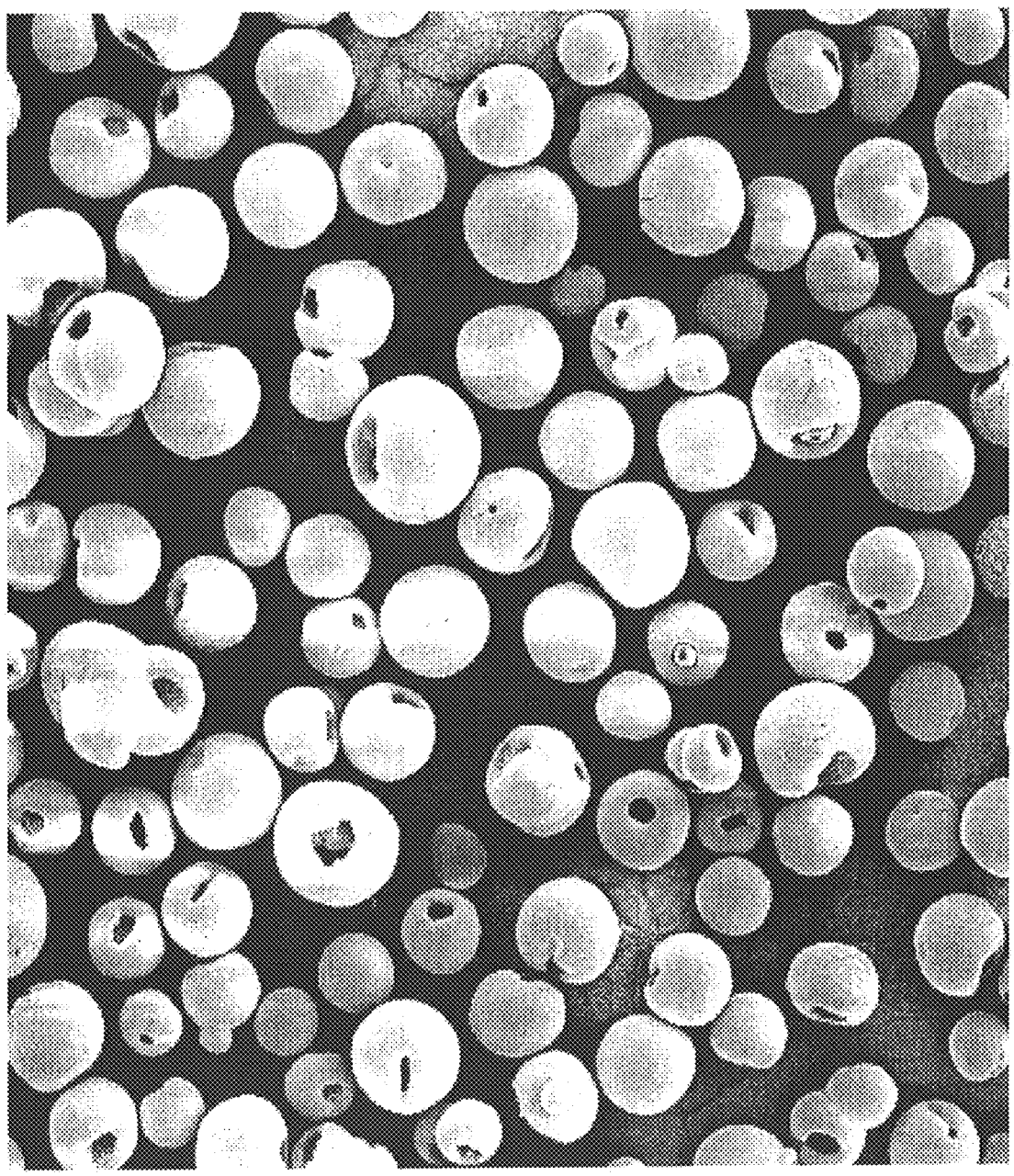
FIG. 10 is an electron microscope photograph (at a magnification of 150 times) showing a zeolite-containing catalyst of Comparative Example 1.
Figure 11:
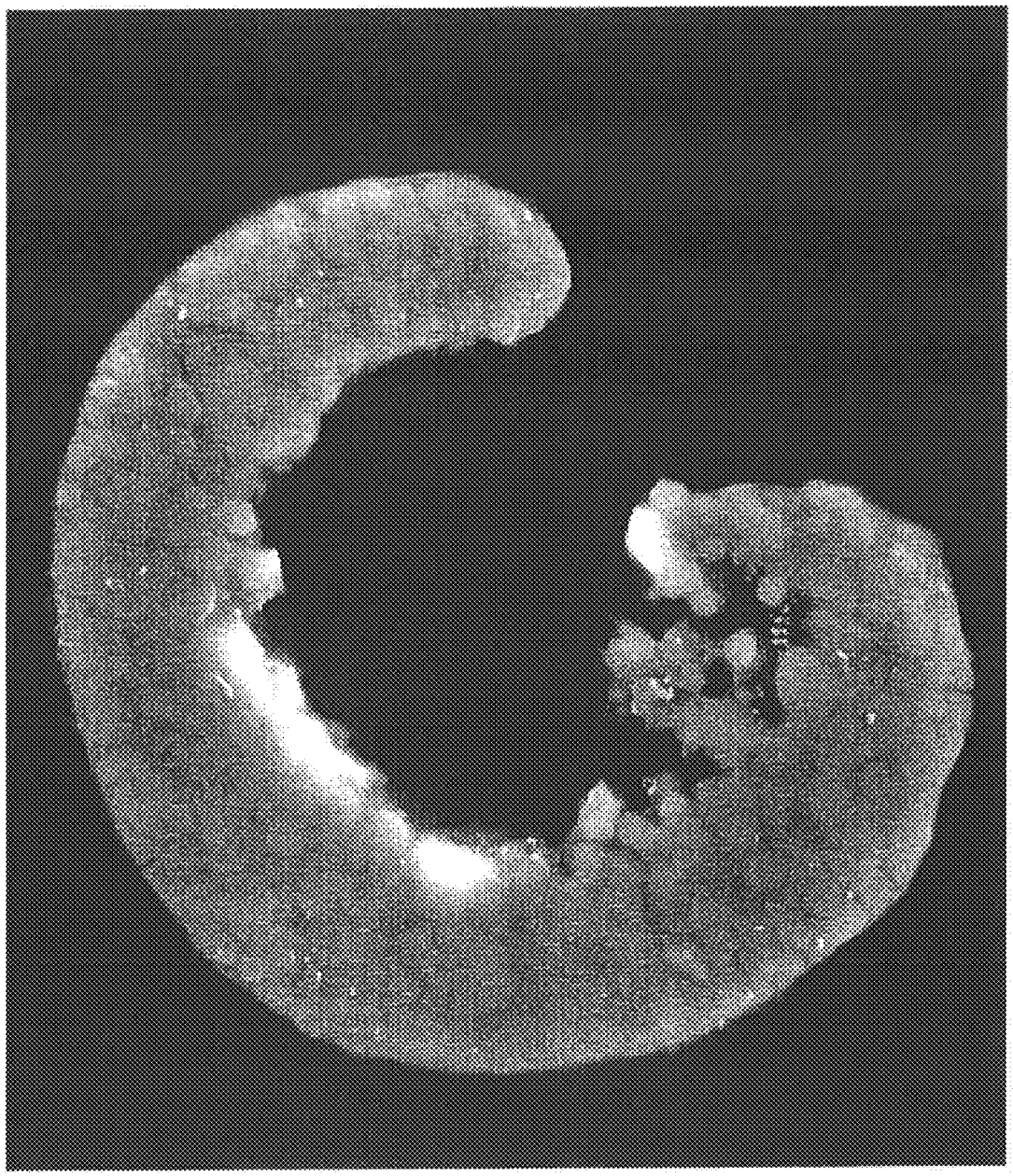
FIG. 11 is an electron microscope photograph (at a magnification of 1600 times) showing a particle cross-section of the zeolite-containing catalyst of Comparative Example 1.

On the zeolite-containing catalyst thus obtained, the above various physical properties in the shape after the calcination and ion-exchanging were measured. The measurement values are shown in Table 4. In addition, the electron microscope photograph of the catalyst particle is shown in FIG. 10 and the electron microscope photograph of the catalyst particle cross-section is shown in FIG. 11.

Comparative Example 2

A zeolite-containing catalyst was prepared in the same manner as in Example 2 except that ammonium nitrate was not added to the raw material slurry.

Figure 12:
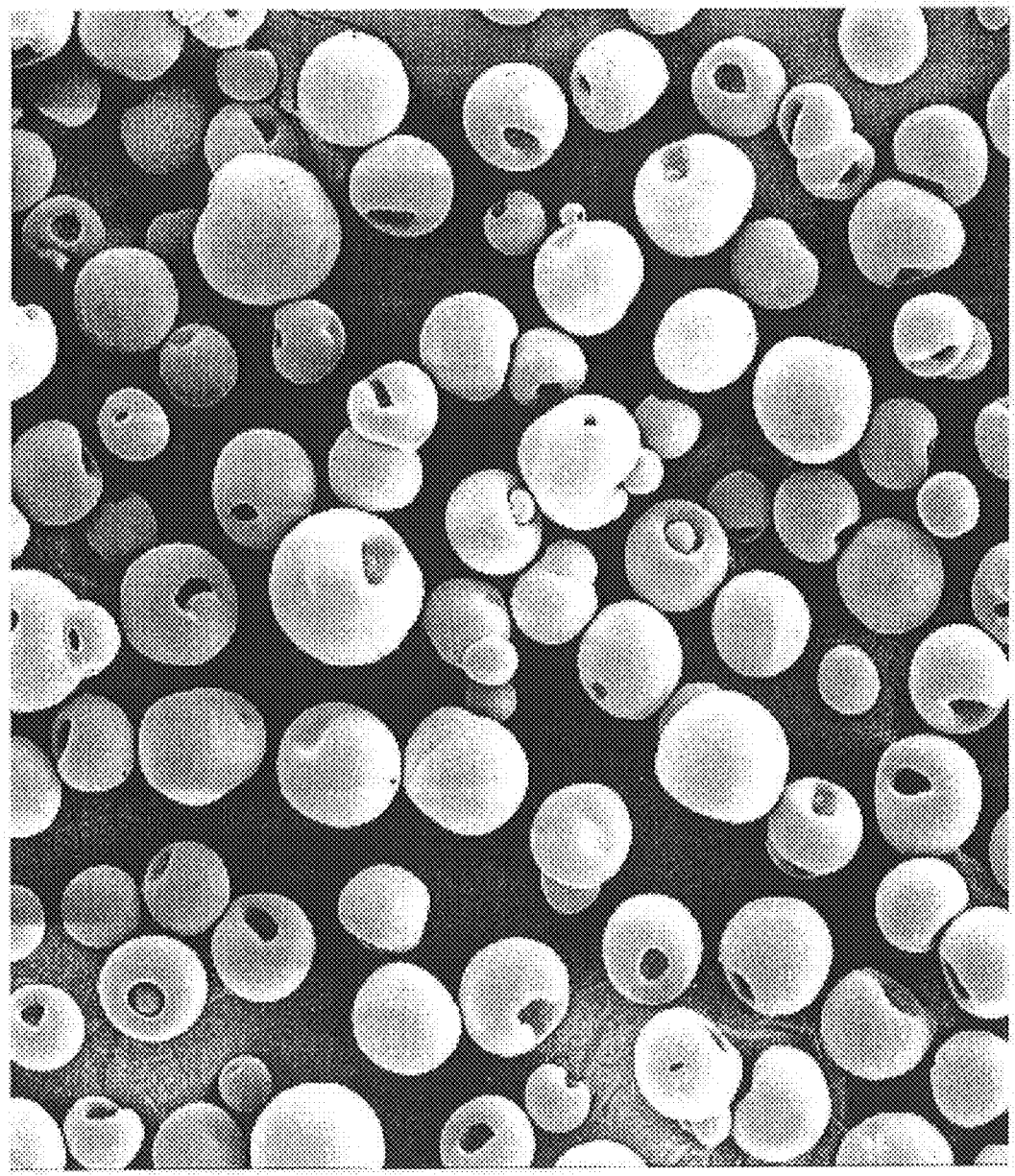
FIG. 12 is an electron microscope photograph (at a magnification of 150 times) showing a zeolite-containing catalyst of Comparative Example 2.
Figure 13:
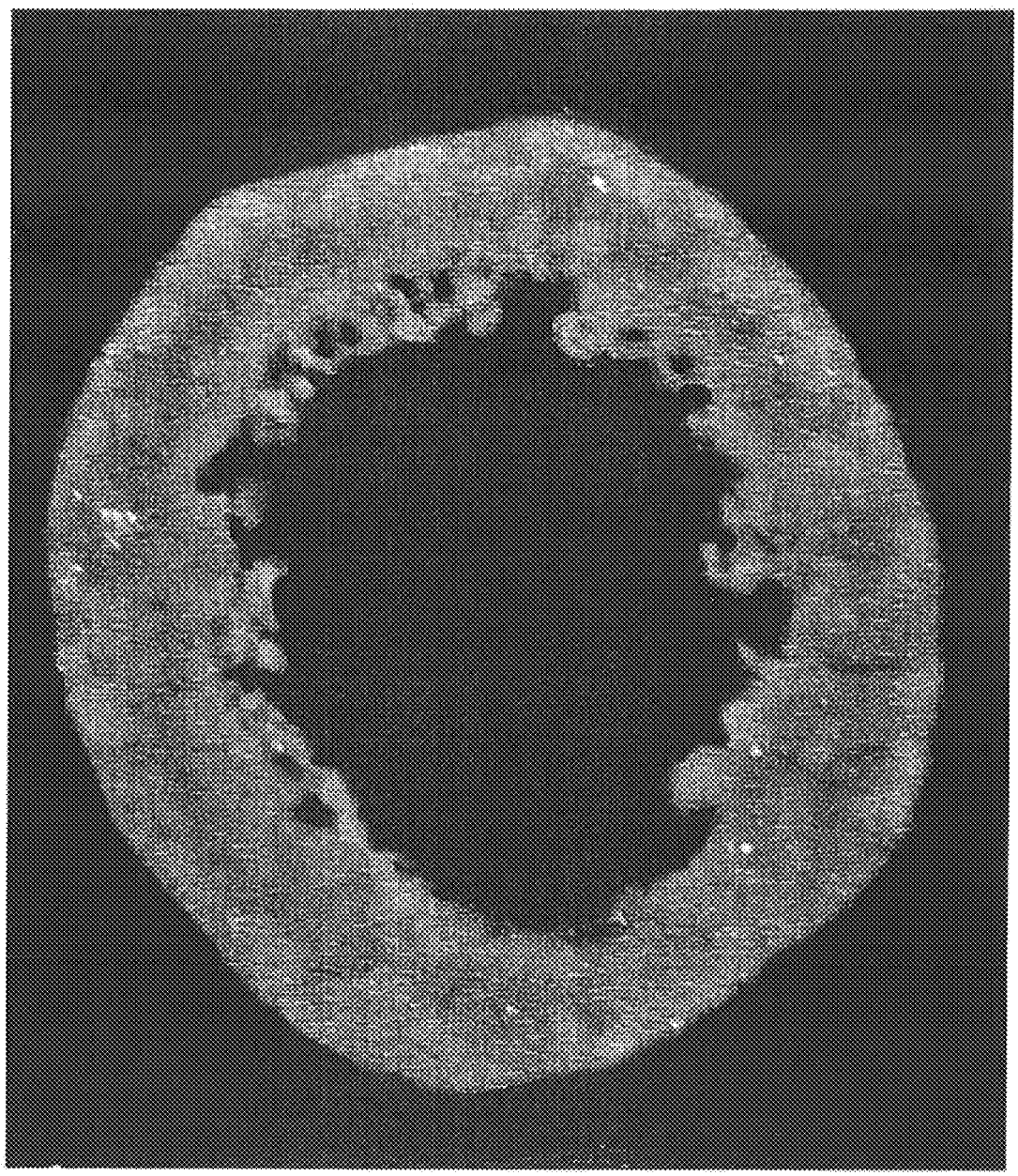
FIG. 13 is an electron microscope photograph (at a magnification of 1500 times) showing a particle cross-section of the zeolite-containing catalyst of Comparative Example 2.

On the zeolite-containing catalyst thus obtained, the above various physical properties in the shape after the calcination and ion-exchanging were measured. The measurement values are shown in Table 4. In addition, the electron microscope photograph of the catalyst particle is shown in FIG. 12 and the electron microscope photograph of the catalyst particle cross-section is shown in FIG. 13.

Comparative Example 3

A zeolite-containing catalyst was prepared in the same manner as in Example 3 except that ammonium nitrate was not added to the raw material slurry.

Figure 14:
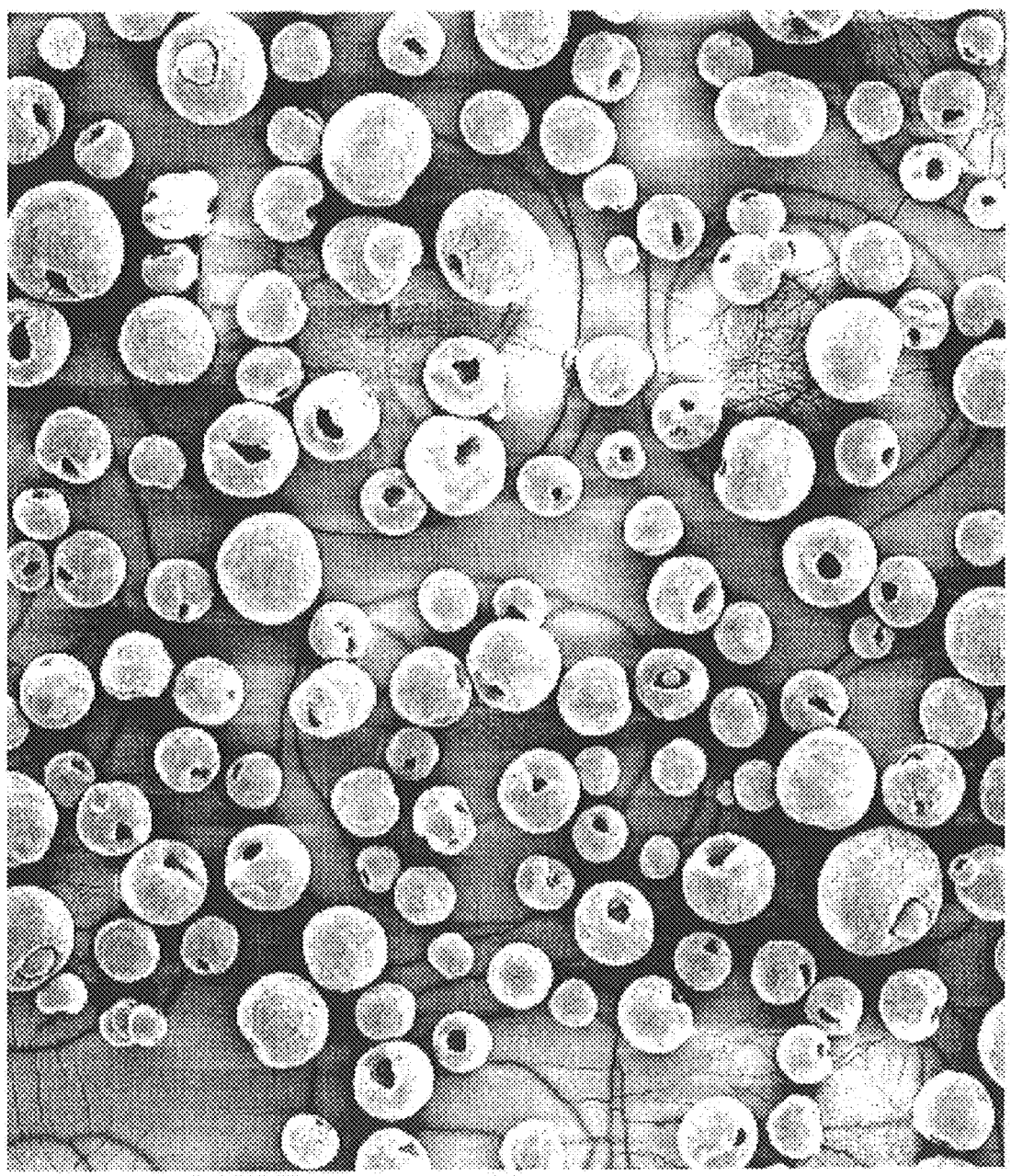
FIG. 14 is an electron microscope photograph (at a magnification of 150 times) showing a zeolite-containing catalyst of Comparative Example 3.
Figure 15:
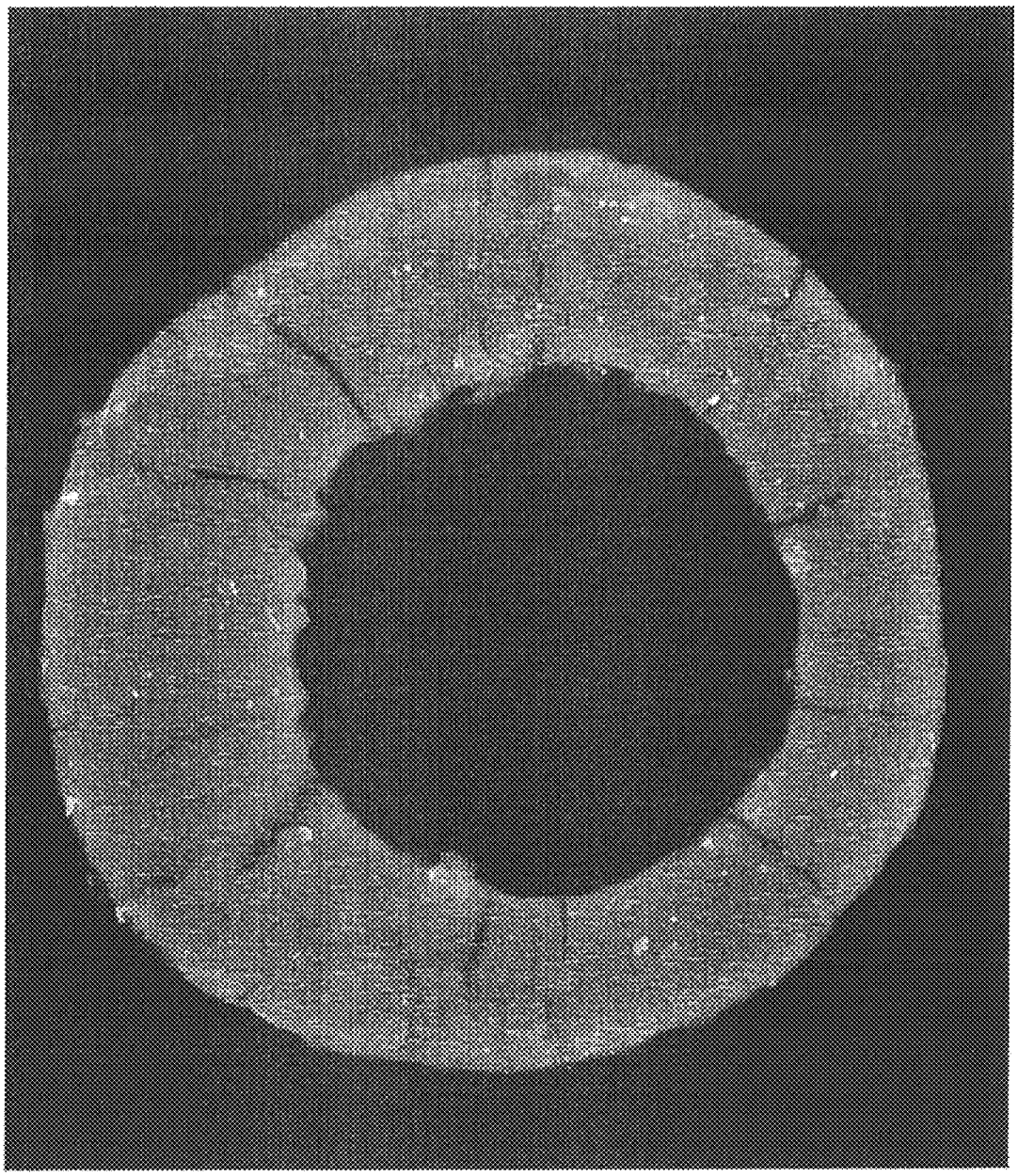
FIG. 15 is an electron microscope photograph (at a magnification of 1500 times) showing a particle cross-section of the zeolite-containing catalyst of Comparative Example 3.

On the zeolite-containing catalyst thus obtained, the above various physical properties in the shape after the calcination and ion-exchanging were measured. The measurement values are shown in Table 4. In addition, the electron microscope photograph of the catalyst particle is shown in FIG. 14 and the electron microscope photograph of the catalyst particle cross-section is shown in FIG. 15.

Comparative Example 4

A zeolite-containing catalyst was prepared in the same manner as in Example 1 except for changing the addition amount of ammonium nitrate to 1.5 g in the preparation step of the raw material slurry.

On the zeolite-containing catalyst thus obtained, the above various physical properties in the shape after the calcination and ion-exchanging were measured. The measurement values are shown in Table 4.

Comparative Example 5

A zeolite-containing catalyst was prepared in the same manner as in Example 1 except for changing the addition amount of ammonium nitrate to 1800 g in the preparation step of the raw material slurry.

On the zeolite-containing catalyst thus obtained, the above various physical properties in the shape after the calcination and ion-exchanging were measured. The measurement values are shown in Table 4.

Comparative Example 6

A zeolite-containing catalyst was prepared in the same manner as in Example 2 except that, in order to reduce the average particle diameter of the zeolite-containing catalyst, the rotation number of the rotating disk in spray drying the raw material slurry in the drying step was increased.

On the zeolite-containing catalyst thus obtained, the above various physical properties in the shape after the calcination and ion-exchanging were measured. The measurement values are shown in Table 4. The zeolite-containing catalyst had an average particle diameter of 12 μm.

Comparative Example 7

A zeolite-containing catalyst was prepared in the same manner as in Example 2 except that, in order to increase the average particle diameter of the zeolite-containing catalyst, the rotation number of the rotating disk in spray drying the raw material slurry and the feed amount of the raw material slurry in the drying step were decreased.

On the zeolite-containing catalyst thus obtained, the above various physical properties in the shape after the calcination and ion-exchanging were measured. The measurement values are shown in Table 4. The zeolite-containing catalyst had an average particle diameter of 386 μm.

Comparative Example 8

A catalyst was prepared according to Example 1 of Japanese Patent Laid-Open No. 10-146529. Firstly, a mixture slurry was prepared by mixing an ultrastable Y-type zeolite (produced by Tosoh Corporation), gibbsite having a particle diameter of 1 to 2 μm (aluminum hydroxide, Alcoa), Georgia kaolin, a LUDOX silica sol (HS-40, produced by DuPont, the $SiO_2$ content rate: 40% by mass) and purified water in the amount described in Example 1 of the patent. Thereafter, an aqueous solution was prepared by mixing sulfuric acid (produced by Wako Pure Chemical Industries, Ltd., special grade reagent) and aluminum sulfate 15-hydrate (produced by Wako Pure Chemical Industries, Ltd., special grade reagent, the same shall apply hereinafter) in the amount described in Example 1 of the patent. To the solution was added an aqueous solution of sodium silicate (produced by PQ Corp., "N" brand, the $SiO_2$ content rate: 28.8% by mass, the $Na_2O$ content rate: 8.9% by mass) in the amount described in Example 1 of the patent. Further, to the resulting solution was added an aqueous solution of aluminum sulfate 15-hydrate of the amount described in Example 1 of the patent. Finally, to the resulting solution was added the firstly prepared mixture slurry to obtain a raw material slurry.

The raw material slurry was spray dried, and the resulting dried powders were washed with hot water at 85° C. and ion-exchanged with an aqueous solution of 12% by mass of ammonium sulfate at 85° C. and then washed with water, followed by finally calcining at 550° C. for 2 hours.

Figure 16:
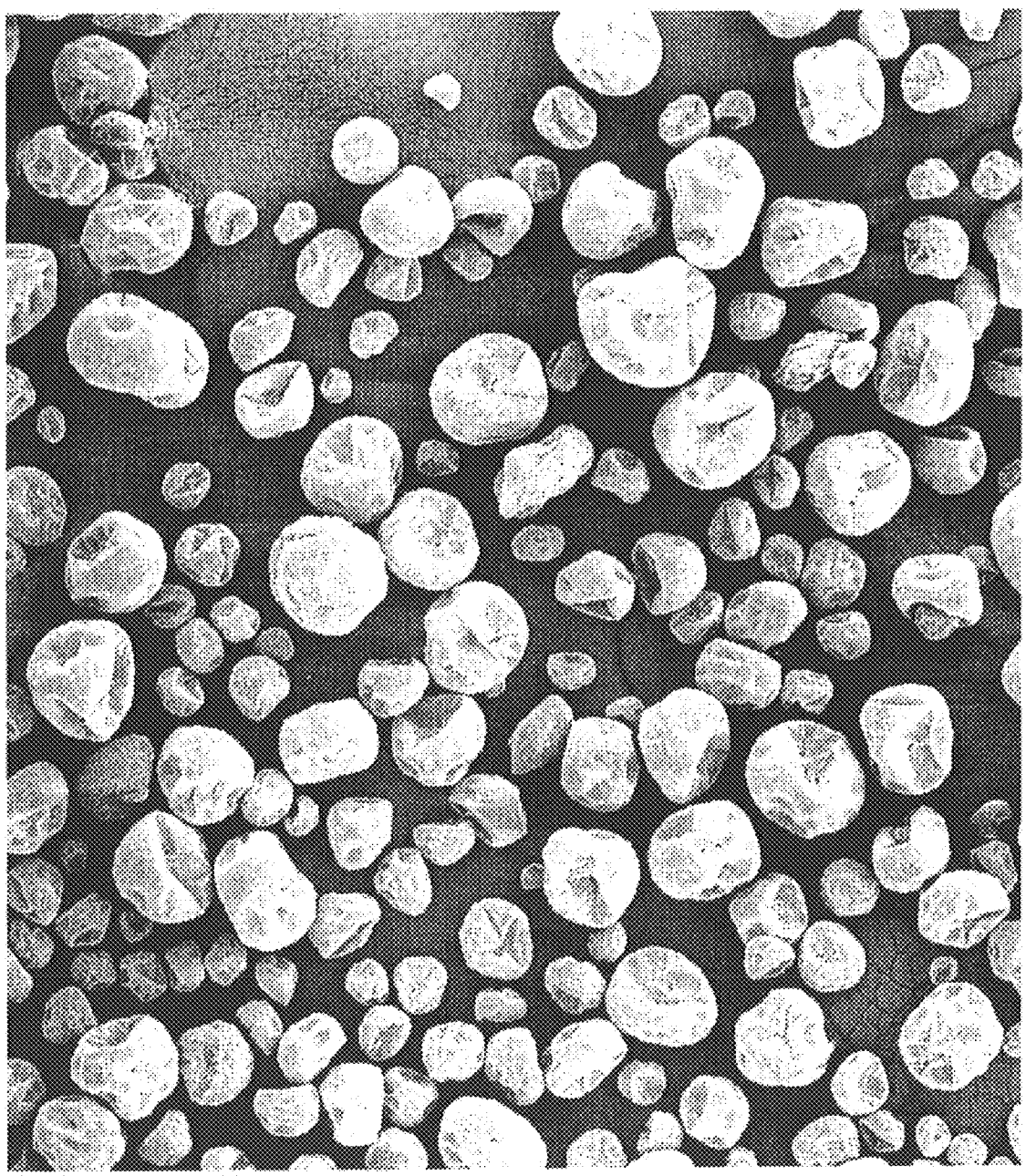
FIG. 16 is an electron microscope photograph (at a magnification of 150 times) showing a zeolite-containing catalyst of Comparative Example 8.
Figure 17:
FIG. 17 is an electron microscope photograph (at a magnification of 1500 times) showing a particle cross-section of the zeolite-containing catalyst of Comparative Example 8.

On the catalyst thus obtained, the above various physical properties were measured. The measurement values are shown in Table 4. In addition, the electron microscope photograph of the catalyst particle is shown in FIG. 16 and the electron microscope photograph of the catalyst particle cross-section is shown in FIG. 17.

In addition, for reference, a part of the dried powders was collected and the sodium content before ion-exchange was measured to be 5.36% by mass.

Comparative Example 9

A zeolite-containing catalyst was prepared in the same manner as in Comparative Example 8 except that, in order to compare with the reaction performance (Example 31) of the zeolite-containing catalyst obtained in Example 17, the zeolite which is an active component was changed to MFI-type ZSM-5 in which the molar ratio $SiO_2/Al_2O_3$ is 27, which was used in Example 17.

The zeolite-containing catalyst thus obtained was subjected to steaming treatment in the same manner as in Example 27. The fluidized bed reaction was carried out using 22.9 g of the catalyst in the same manner as in Example 27. The process of the ethylene conversion rate at each reaction time is shown in FIG. 19.

In addition, for reference, a part of the dried powders was collected and the sodium content before ion-exchange was measured to be 5.36% by mass.

As is clear from the results shown in Tables 1 to 3, the zeolite-containing catalyst of the present invention had a dense structure in which the void area of the particle cross-section is small and was excellent in mechanical strength. The particle had a smooth spherical surface and had an angle of repose as measured by the above method, which is an indicator of fluidity, in the range from 25 to 30°. This means that the particle shows the most preferable fluidity, as described in Page 42 of "Fluidized Bed Handbook" (edited by the Association of Powder Process Industry & Engineering, Japan, and published by Baifukan on Mar. 25, 1999). These facts show that the zeolite-containing catalyst of the present invention has excellent shape, fluidity and strength as a fluidized bed reaction catalyst.

Further, as is clear from the results shown in FIGS. 18 and 19, when the zeolite-containing catalyst of the present invention is used as a catalyst for the fluidized bed reaction for producing propylene from a reaction raw material containing ethylene (Examples 27 to 31), it is possible to stably produce propylene in good yield.

Especially, when a catalyst containing a phosphorous-modified zeolite is used (Example 28), it exhibited higher activity compared to a catalyst containing a H+ type zeolite (Example 27) even after subjecting to the same steaming treatment, and deterioration with an elapse of time due to coking was suppressed.

In addition, a zeolite-containing catalyst prepared using a colloidal silica as in the case of Example 17 exhibited sufficiently high activity by only calcining without ion-exchanging, because the sodium amount in the catalyst composition is extremely small (Example 29). This leads to the simplification of the catalyst production step and is extremely useful in industrial practical use.

On the other hand, as is clear from the results shown in Table 4, the zeolite-containing catalysts of Comparative Examples (Comparative Examples 1 to 9) including well-known ones were inferior in mechanical strength because the catalysts had many void portions inside the particle and were inferior in fluidity because the angle of repose was extremely large as in the case of Comparative Example 6.

In addition, in the zeolite-containing catalyst prepared using a silica sol containing much water glass, it was difficult to obtain a highly active catalyst because sodium was insufficiently removed even by ion-exchange (Comparative Example 9).

TABLE 1

|  |  |  | Ex. 1 | Ex. 2 | Ex. 3 | Ex. 4 |
|---|---|---|---|---|---|---|
| Raw material components | Water-soluble compound |  | Ammonium nitrate | Ammonium nitrate | Ammonium nitrate | Ammonium nitrate |
|  | Zeolite |  | MFI-type ZSM-5 | MFI-type ZSM-5 | MFI-type ZSM-5 | MFI-type ZSM-5 |
|  | $SiO_2/Al_2O_3$ | [mol ratio] | 280 | 27 | 1000 | 42 |
|  | Water-soluble compound/Colloidal silica | [wt ratio] | 0.33 | 0.33 | 0.33 | 0.33 |
|  | Colloidal silica | [g] | 2000 | 2000 | 2000 | 2000 |
|  | Nitric acid | [g] | 40 | 40 | 40 | 40 |
|  | Water-soluble compound | [g] | 100 | 100 | 100 | 100 |
|  | Zeolite | [g] | 300 | 300 | 300 | 300 |
|  | Viscosity of raw material slurry | [cP] | 5 | 5 | 6 | 5 |
|  | pH of raw material slurry |  | 1.1 | 0.9 | 1.2 | 1.2 |
| Catalyst physical properties | Average particle diameter | [μm] | 53 | 50 | 52 | 54 |
|  | Zeolite content rate | [wt %] | 50 | 50 | 50 | 50 |
|  | Silica content rate | [wt %] | 50 | 50 | 50 | 50 |
|  | Other components content rate | [wt %] | 0 | 0 | 0 | 0 |
|  | Angle of repose | [°] | 25 | 25 | 25 | 25 |
|  | Void area ratio of cross-section | [%] | 3 | 6 | 4 | 5 |
|  | Attrition loss | [wt %] | 0.1 | 0.2 | 0.6 | 0.5 |
|  | Na content of calcined product | [wt %] | 0.06 | 0.06 | 0.06 | 0.06 |
|  | Na content in ion-exchanged product | [ppm] | 52 | 55 | 60 | 46 |

|  |  |  | Ex. 5 | Ex. 6 | Ex. 7 | Ex. 8 |
|---|---|---|---|---|---|---|
| Raw material components | Water-soluble compound |  | Ammonium acetate | Ammonium sulfate | Ammonium chloride | Ammonium carbonate |
|  | Zeolite |  | MFI-type ZSM-5 | MFI-type ZSM-5 | MFI-type ZSM-5 | MFI-type ZSM-5 |
|  | $SiO_2/Al_2O_3$ | [mol ratio] | 280 | 280 | 80 | 80 |
|  | Water-soluble compound/Colloidal silica | [wt ratio] | 0.33 | 0.33 | 0.24 | 0.20 |
|  | Colloidal silica | [g] | 2000 | 795 | 2000 | 2000 |
|  | Nitric acid | [g] | 40 | 40 | 40 | 40 |
|  | Water-soluble compound | [g] | 100 | 100 | 72 | 60 |
|  | Zeolite | [g] | 300 | 300 | 300 | 300 |
|  | Viscosity of raw material slurry | [cP] | 5 | 6 | 5 | 6 |
|  | pH of raw material slurry |  | 1.0 | 1.7 | 1.0 | 1.3 |
| Catalyst physical properties | Average particle diameter | [μm] | 52 | 52 | 54 | 53 |
|  | Zeolite content rate | [wt %] | 50 | 50 | 50 | 50 |
|  | Silica content rate | [wt %] | 50 | 50 | 50 | 50 |
|  | Other components content rate | [wt %] | 0 | 0 | 0 | 0 |
|  | Angle of repose | [°] | 25 | 27 | 26 | 25 |
|  | Void area ratio of cross-section | [%] | 10 | 10 | 11 | 12 |
|  | Attrition loss | [wt %] | 1.2 | 1.4 | 1.8 | 1.0 |
|  | Na content of calcined product | [wt %] | 0.06 | 0.04 | 0.06 | 0.06 |
|  | Na content in ion-exchanged product | [ppm] | 45 | 32 | 50 | 38 |

TABLE 2

|  |  |  | Ex. 9 | Ex. 10 | Ex. 11 | Ex. 12 |
|---|---|---|---|---|---|---|
| Raw material components | Water-soluble compound |  | Aluminium nitrate 9-hydrate | Sodium nitrate | Ammonium nitrate | Ammonium nitrate |
|  | Zeolite |  | MFI-type ZSM-5 | MFI-type ZSM-5 | MFI-type ZSM-5 | MFI-type ZSM-5 |
|  | $SiO_2/Al_2O_3$ | [mol ratio] | 280 | 27 | 27 | 27 |
|  | Water-soluble compound/Colloidal silica | [wt ratio] | 0.82 | 0.35 | 0.33 | 0.33 |
|  | Colloidal silica | [g] | 1800 | 2000 | 2000 | 2000 |
|  | Nitric acid | [g] | 40 | 40 | 40 | 40 |
|  | Water-soluble compound | [g] | 221 | 106 | 100 | 100 |
|  | Zeolite | [g] | 300 | 300 | 300 | 300 |
|  | Viscosity of raw material slurry | [cP] | 6 | 6 | 5 | 5 |
|  | pH of raw material slurry |  | 0.9 | 0.8 | 0.9 | 0.9 |
| Catalyst physical properties | Average particle diameter | [μm] | 53 | 55 | 21 | 87 |
|  | Zeolite content rate | [wt %] | 50 | 47 | 50 | 50 |
|  | Silica content rate | [wt %] | 45 | 47 | 50 | 50 |
|  | Other components content rate | [wt %] | 5($Al_2O_3$) | 6($Na_2O$) | 0 | 0 |
|  | Angle of repose | [°] | 26 | 26 | 29 | 26 |
|  | Void area ratio of cross-section | [%] | 18 | 16 | 5 | 6 |
|  | Attrition loss | [wt %] | 2.5 | 2.8 | 0.3 | 0.2 |
|  | Na content of calcined product | [wt %] | 0.06 | 4.62 | 0.06 | 0.06 |
|  | Na content in ion-exchanged product | [ppm] | 35 | 14600 | 40 | 54 |

|  |  |  | Ex. 13 | Ex. 14 | Ex. 15 | Ex. 16 |
|---|---|---|---|---|---|---|
| Raw material components | Water-soluble compound |  | Ammonium nitrate | Ammonium nitrate | Ammonium nitrate | Ammonium nitrate |
|  | Zeolite |  | MFI-type ZSM-5 | MFI-type ZSM-5 | MFI-type ZSM-5 | MFI-type ZSM-5 |
|  | $SiO_2/Al_2O_3$ | [mol ratio] | 27 | 80 | 80 | 80 |
|  | Water-soluble compound/Colloidal silica | [wt ratio] | 0.33 | 0.03 | 0.1 | 4.8 |
|  | Colloidal silica | [g] | 2000 | 2000 | 2000 | 2000 |
|  | Nitric acid | [g] | 40 | 40 | 40 | 40 |
|  | Water-soluble compound | [g] | 100 | 10 | 30 | 1440 |
|  | Zeolite | [g] | 300 | 300 | 300 | 300 |
|  | Viscosity of raw material slurry | [cP] | 5 | 6 | 6 | 6 |
|  | pH of raw material slurry |  | 0.9 | 1.0 | 1.0 | 0.9 |
| Catalyst physical properties | Average particle diameter | [μm] | 293 | 56 | 54 | 55 |
|  | Zeolite content rate | [wt %] | 50 | 50 | 50 | 50 |
|  | Silica content rate | [wt %] | 50 | 50 | 50 | 50 |
|  | Other components content rate | [wt %] | 0 | 0 | 0 | 0 |
|  | Angle of repose | [°] | 26 | 26 | 25 | 26 |
|  | Void area ratio of cross-section | [%] | 12 | 26 | 18 | 15 |
|  | Attrition loss | [wt %] | 1.3 | 2.5 | 1.5 | 2.8 |
|  | Na content of calcined product | [wt %] | 0.06 | 0.06 | 0.06 | 0.06 |
|  | Na content in ion-exchanged product | [ppm] | 57 | 58 | 65 | 50 |

TABLE 3

|  |  |  | Ex. 17 | Ex. 18 | Ex. 19 | Ex. 20 | Ex. 21 |
|---|---|---|---|---|---|---|---|
| Raw material components | Water-soluble compound |  | Ammonium nitrate | Ammonium nitrate | Ammonium nitrate | Ammonium nitrate | Ammonium nitrate |
|  | Zeolite |  | MFI-type ZSM-5 | MFI-type ZSM-5 | MFI-type ZSM-5 | BEA-type Beta | MFI-type ZSM-5 |
|  | $SiO_2/Al_2O_3$ | [mol ratio] | 27 | 80 | 80 | 25 | 42 |
|  | Water-soluble compound/Colloidal silica | [wt ratio] | 0.33 | 0.33 | 0.33 | 0.33 | 0.33 |
|  | Colloidal silica | [g] | 1235 | 3800 | 1200 | 2800 | 2000 |
|  | Nitric acid | [g] | 40 | 60 | 24 | 56 | 40 |
|  | Water-soluble compound | [g] | 140 | 188 | 60 | 140 | 100 |
|  | Zeolite | [g] | 180 | 30 | 420 | 180 | 300 |
|  | Viscosity of raw material slurry | [cP] | 6 | 5 | 8 | 5 | 6 |
|  | pH of raw material slurry |  | 0.9 | 1.5 | 0.7 | 0.9 | 1.2 |
| Catalyst physical properties | Average particle diameter | [μm] | 51 | 54 | 53 | 53 | 52 |
|  | Zeolite content rate | [wt %] | 30 | 5 | 70 | 30 | 50 |
|  | Silica content rate | [wt %] | 70 | 95 | 30 | 70 | 50 |
|  | Other components content rate | [wt %] | 0 | 0 | 0 | 0 | 0 |

TABLE 3-continued

|  |  |  | Ex. 22 | Ex. 23 | Ex. 24 | Ex. 25 |
|---|---|---|---|---|---|---|
| | Angle of repose | [°] | 25 | 25 | 28 | 25 | 25 |
| | Void area ratio of cross-section | [%] | 8 | 5 | 25 | 8 | 8 |
| | Attrition loss | [wt %] | 0.3 | 0.2 | 2.8 | 0.8 | 0.6 |
| | Na content of calcined product | [wt %] | 0.002 | 0.12 | 0.04 | 0.09 | 0.06 |
| | Na content in ion-exchanged product | [ppm] | 14 | 98 | 18 | 67 | 50 |

| | | | Ex. 22 | Ex. 23 | Ex. 24 | Ex. 25 |
|---|---|---|---|---|---|---|
| Raw material components | Water-soluble compound | | Ammonium nitrate | Ammonium nitrate | Ammonium nitrate | Ammonium nitrate |
| | Zeolite | | MFI-type ZSM-5 | MFI-type ZSM-5 | MFI-type ZSM-5 | MFI-type ZSM-5 |
| | $SiO_2/Al_2O_3$ | [mol ratio] | 39 | 27 | 27 | 27 |
| | Water-soluble compound/Colloidal silica | [wt ratio] | 0.20 | 0.33 | 0.50 | 0.33 |
| | Colloidal silica | [g] | 2000 | 1800 (*1) | 2000 | 1680 (*2) |
| | Nitric acid | [g] | 40 | 98 | 40 | 160 |
| | Water-soluble compound | [g] | 60 | 75 | 150 | 59 |
| | Zeolite | [g] | 300 (*3) | 300 | 300 | 300 |
| | Viscosity of raw material slurry | [cP] | 4 | 5 | 5 | 8 |
| | pH of raw material slurry | | 1.2 | 1.1 | 1.0 | 0.5 |
| Catalyst physical properties | Average particle diameter | [μm] | 51 | 52 | 52 | 52 |
| | Zeolite content rate | [wt %] | 50 | 48 | 50 | 46.5 |
| | Silica content rate | [wt %] | 50 | 48 | 50 | 46.5 |
| | Other components content rate | [wt %] | 0 | 4($Na_2O$) | 0 | 7($Na_2O$) |
| | Angle of repose | [°] | 28 | 26 | 25 | 30 |
| | Void area ratio of cross-section | [%] | 5 | 15 | 5 | 25 |
| | Attrition loss | [wt %] | 0.2 | 0.8 | 0.3 | 2.3 |
| | Na content of calcined product | [wt %] | 0.06 | — | 0.06 | — |
| | Na content in ion-exchanged product | [ppm] | 52 | 150 | 62 | 260 |

(*1) Represents the total of the colloidal silica and the water glass (the silica component of the colloidal silica is 75% by mass and the silica component of the water glass is 25% by mass)
(*2) Represents the total of the colloidal silica and the water glass (the silica component of the colloidal silica is 60% by mass and the silica component of the water glass is 40% by mass)
(*3) Represents the zeolite amount contained in the raw material zeolite slurry.

TABLE 4

| | | | Com. Ex. 1 | Com. Ex. 2 | Com. Ex. 3 | Com. Ex. 4 | Com. Ex. 5 |
|---|---|---|---|---|---|---|---|
| Raw material components | Water-soluble compound | | — | — | — | Ammonium nitrate | Ammonium nitrate |
| | Zeolite | | MFI-type ZSM-5 | MFI-type ZSM-5 | MFI-type ZSM-5 | MFI-type ZSM-5 | MFI-type ZSM-5 |
| | $SiO_2/Al_2O_3$ | [mol ratio] | 280 | 27 | 1000 | 280 | 280 |
| | Water-soluble compound/Colloidal silica | [wt ratio] | — | — | — | 0.005 | 6.0 |
| | Colloidal silica | [g] | 2000 | 2000 | 2000 | 2000 | 2000 |
| | Nitric acid | [g] | 40 | 40 | 40 | 40 | 40 |
| | Water-soluble compound | [g] | 0 | 0 | 0 | 1.5 | 1800 |
| | Zeolite | [g] | 300 | 300 | 300 | 300 | 300 |
| | Viscosity of raw material slurry | [cP] | 5 | 6 | 5 | 5 | 6 |
| | pH of raw material slurry | | 1.1 | 1.2 | 1.0 | 0.9 | 1.0 |
| Catalyst physical properties | Average particle diameter | [μm] | 51 | 53 | 53 | 50 | 54 |
| | Zeolite content rate | [wt %] | 50 | 50 | 50 | 50 | 50 |
| | Silica content rate | [wt %] | 50 | 50 | 50 | 50 | 50 |
| | Other components content rate | [wt %] | 0 | 0 | 0 | 0 | 0 |
| | Angle of repose | [°] | 27 | 28 | 27 | 27 | 28 |
| | Void area ratio of cross-section | [%] | 35 | 34 | 40 | 36 | 35 |
| | Attrition loss | [wt %] | 6.7 | 5.6 | 25 | 6.5 | 5.3 |
| | Na content of calcined product | [wt %] | 0.06 | 0.06 | 0.06 | 0.06 | 0.06 |
| | Na content in ion-exchanged product | [ppm] | 53 | 32 | 57 | 56 | 60 |

| | | | Com. Ex. 6 | Com. Ex. 7 | Com. Ex. 8 | Com. Ex. 9 |
|---|---|---|---|---|---|---|
| Raw material components | Water-soluble compound | | Ammonium nitrate | Ammonium nitrate | Aluminum sulfate 15-hydrate | Aluminum sulfate 15-hydrate |
| | Zeolite | | MFI-type ZSM-5 | MFI-type ZSM-5 | USY | MFI-type ZSM-5 |
| | $SiO_2/Al_2O_3$ | [mol ratio] | 27 | 27 | 5 | 27 |
| | Water-soluble compound/Colloidal silica | [wt ratio] | 0.33 | 0.33 | 3.9 | 3.9 |
| | Colloidal silica | [g] | 2000 | 2000 | 13220 (*1) | 13220 (*1) |
| | Nitric acid | [g] | 40 | 40 | 2270 (*2) | 2270 (*2) |
| | Water-soluble compound | [g] | 100 | 100 | 5590 | 5590 |
| | Zeolite | [g] | 300 | 300 | 3400 | 3400 |

TABLE 4-continued

| | | | | | | |
|---|---|---|---|---|---|---|
| | Viscosity of raw material slurry | [cP] | 6 | 6 | 6 | 6 |
| | pH of raw material slurry | | 0.9 | 0.9 | 3.2 | 3.2 |
| Catalyst physical properties | Average particle diameter | [μm] | 12 | 386 | 52 | 53 |
| | Zeolite content rate | [wt %] | 50 | 50 | 29 | 29 |
| | Silica content rate | [wt %] | 50 | 50 | 35 | 35 |
| | Other components content rate | [wt %] | 0 | 0 | 36 | 36 |
| | Angle of repose | [°] | 42 | 28 | 32 | 32 |
| | Void area ratio of cross-section | [%] | 8 | 39 | 42 | 40 |
| | Attrition loss | [wt %] | 0.5 | 7.2 | 5.2 | 4.2 |
| | Na content of calcined product | [wt %] | 0.06 | 0.06 | — | — |
| | Na content in ion-exchanged product | [ppm] | 45 | 62 | 420 | 400 |

(*1) Represents the total of the colloidal silica and the water glass (the silica component of the colloidal silica is 34% by mass and the silica component of the water glass is 66% by mass)
(*2) Represents the sulfuric acid amount The present application is based on Japanese Patent Application No. 2008-202806 filed on Aug. 6, 2008, the entire contents of which are incorporated herein by reference.

INDUSTRIAL APPLICABILITY

The zeolite-containing catalyst of the present invention may be suitably used as a catalyst when propylene is produced from a hydrocarbon reaction raw material containing ethylene or the like by a fluidized bed reaction because the catalyst has preferred physical properties as a catalyst for the fluidized bed reaction.

The invention claimed is:

1. A zeolite-containing catalyst which is a particulate catalyst containing zeolite and silica, wherein the catalyst has an average particle diameter of 20 to 300 μm and the ratio of the void area in a cross-section of said particle is 0.3 or less relative to the cross-section area of the particle, wherein said zeolite is an MFI-type zeolite.

2. The zeolite-containing catalyst according to claim 1, wherein said MFI-type zeolite is a ZSM-5 zeolite.

3. The zeolite-containing catalyst according to claim 1, wherein the content ratio of said zeolite in the particulate catalyst is from 0.1 to 0.9 by mass, the content ratio of said silica in the particulate catalyst is from 0.1 to 0.9 by mass, and the total content ratio of said zeolite and said silica in the particulate catalyst is 0.5 or more by mass.

4. A method for producing propylene comprising the step of contacting a zeolite-containing catalyst according to claim 1 with a hydrocarbon and/or an alcohol in a fluidized bed reactor.

5. The zeolite-containing catalyst according to claim 2, wherein the content ratio of said zeolite in the particulate catalyst is from 0.1 to 0.9 by mass, the content ratio of said silica in the particulate catalyst is from 0.1 to 0.9 by mass, and the total content ratio of said zeolite and said silica in the particulate catalyst is 0.5 or more by mass.

6. A method for producing propylene comprising the step of contacting a zeolite-containing catalyst according to claim 2 with a hydrocarbon and/or an alcohol in a fluidized bed reactor.

* * * * *